US011399697B2

(12) United States Patent
Sato

(10) Patent No.: US 11,399,697 B2
(45) Date of Patent: Aug. 2, 2022

(54) BEND INFORMATION COMPUTATION APPARATUS, ENDOSCOPE SYSTEM INCLUDING THE APPARATUS, AND BEND INFORMATION COMPUTATION METHOD

(71) Applicant: OLYMPUS CORPORATION, Tokyo (JP)

(72) Inventor: Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 562 days.

(21) Appl. No.: 16/445,633

(22) Filed: Jun. 19, 2019

(65) Prior Publication Data

US 2020/0000311 A1 Jan. 2, 2020

Related U.S. Application Data

(63) Continuation of application No. PCT/JP2016/087944, filed on Dec. 20, 2016.

(51) Int. Cl.
| | |
|---|---|
| *A61B 1/00* | (2006.01) |
| *G01B 11/24* | (2006.01) |
| *A61B 34/20* | (2016.01) |
| *A61B 1/005* | (2006.01) |
| *A61B 1/07* | (2006.01) |

(52) U.S. Cl.
CPC .......... *A61B 1/00006* (2013.01); *A61B 1/005* (2013.01); *A61B 1/07* (2013.01); *G01B 11/24* (2013.01); *A61B 2034/2061* (2016.02)

(58) Field of Classification Search
None
See application file for complete search history.

(56) References Cited

U.S. PATENT DOCUMENTS

| | | | |
|---|---|---|---|
| 2008/0212082 A1* | 9/2008 | Froggatt | G01D 5/35316 356/73.1 |
| 2011/0098533 A1* | 4/2011 | Onoda | A61B 5/065 600/117 |

(Continued)

FOREIGN PATENT DOCUMENTS

| | | |
|---|---|---|
| JP | 4714570 B2 | 6/2011 |
| JP | 2015029831 A | 2/2015 |

(Continued)

OTHER PUBLICATIONS

English translation of International Preliminary Report on Patentability dated Jul. 4, 2019, together with the Written Opinion received in related International Application No. PCT/JP2016/087944.

(Continued)

*Primary Examiner* — John P Leubecker
(74) *Attorney, Agent, or Firm* — Scully, Scott, Murphy & Presser, P.C.

(57) ABSTRACT

Bend information computation apparatus includes: an input unit having detected light quantity information representing a relation between a wavelength in a predetermined wavelength band and a light quantity, the detected light quantity information being acquired using a light guide having at least one light absorber for changing a light quantity of light transmitted through the light guide according to a bent state of the light absorber to detect a light quantity after a change; and an arithmetic operator for computing bend information representing a bend direction and a bend magnitude of each light absorber based on the detected light quantity information, an absorption spectrum of each light absorber, a bend coefficient of each light absorber that varies according to a bend direction and a bend magnitude of each light absorber, and a unique characteristic value of each light absorber (Continued)

including a value for a correction relating to the bend coefficient.

20 Claims, 11 Drawing Sheets

(56) References Cited

U.S. PATENT DOCUMENTS

2016/0073858 A1* 3/2016 Sato .................. A61B 1/00006 600/117
2016/0128552 A1* 5/2016 Tojo ........................ A61B 1/01 600/102

FOREIGN PATENT DOCUMENTS

| JP | 2016007505 A | 1/2016 |
| JP | 2016007506 A | 1/2016 |
| WO | 2016178279 A1 | 11/2016 |
| WO | 2016194059 A1 | 12/2016 |

OTHER PUBLICATIONS

International Search Report dated Mar. 21, 2017 issued in PCT/JP2016/087944.

* cited by examiner

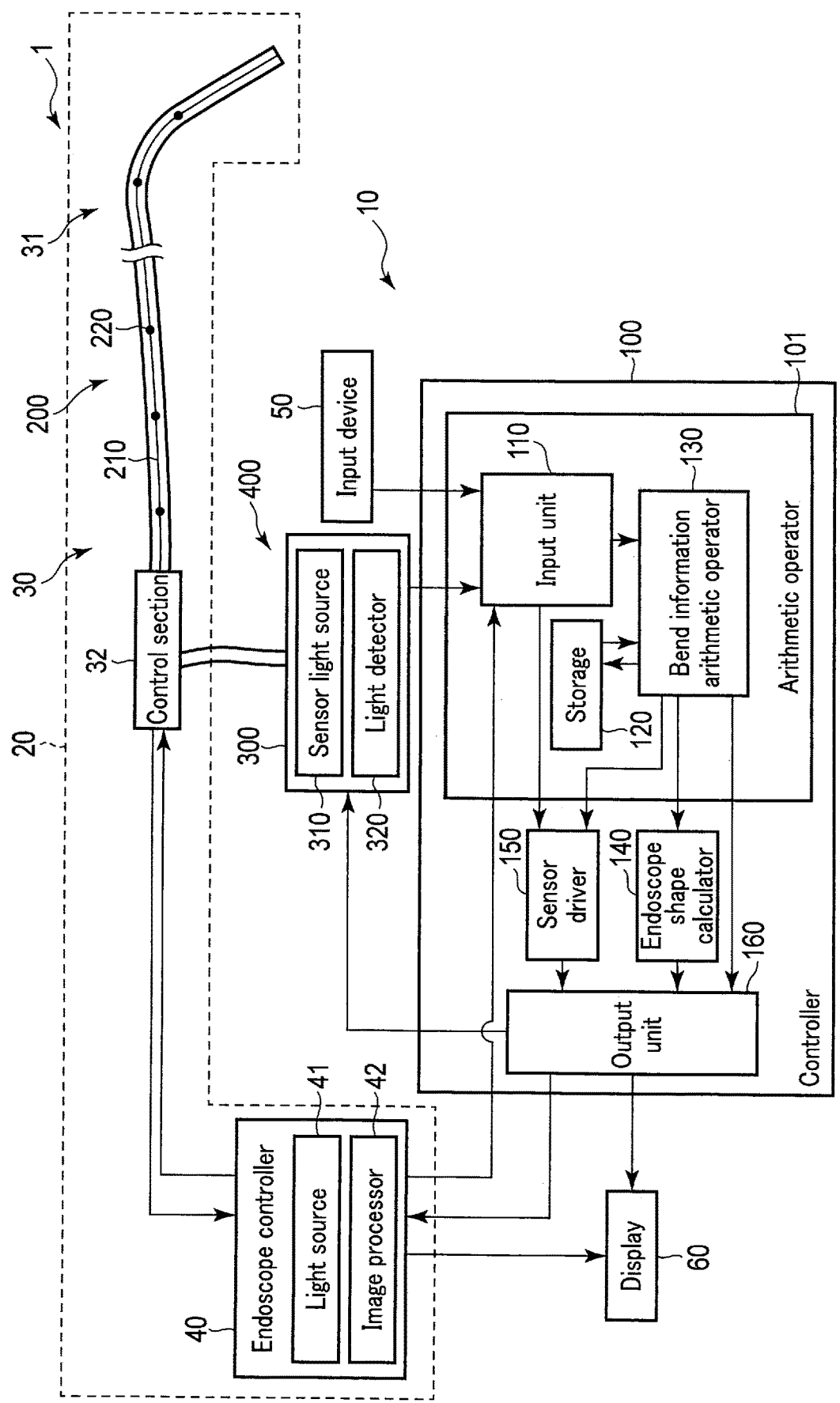
F I G. 1

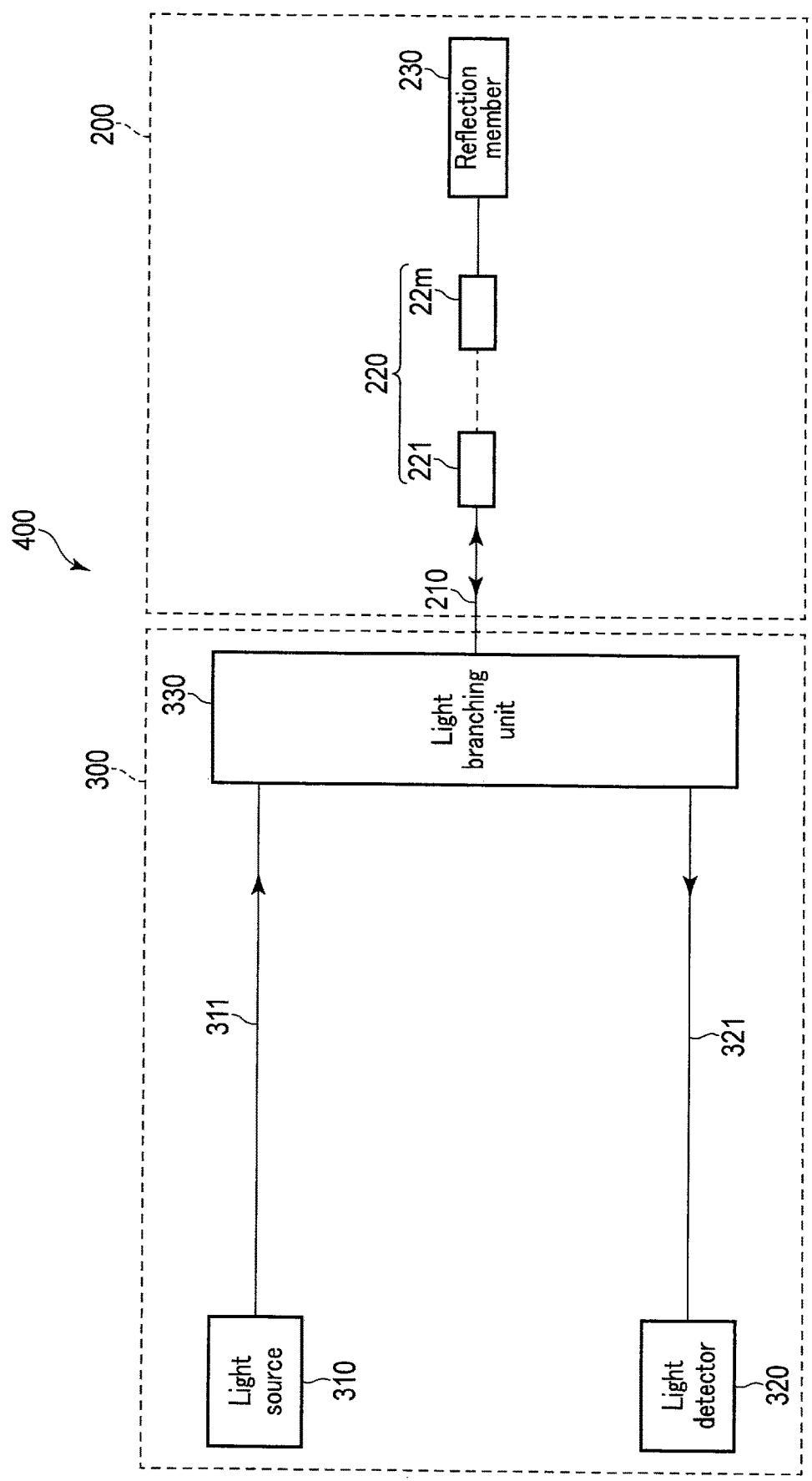
F I G. 2

Configuration (I)

Configuration (II)

Configuration (III)

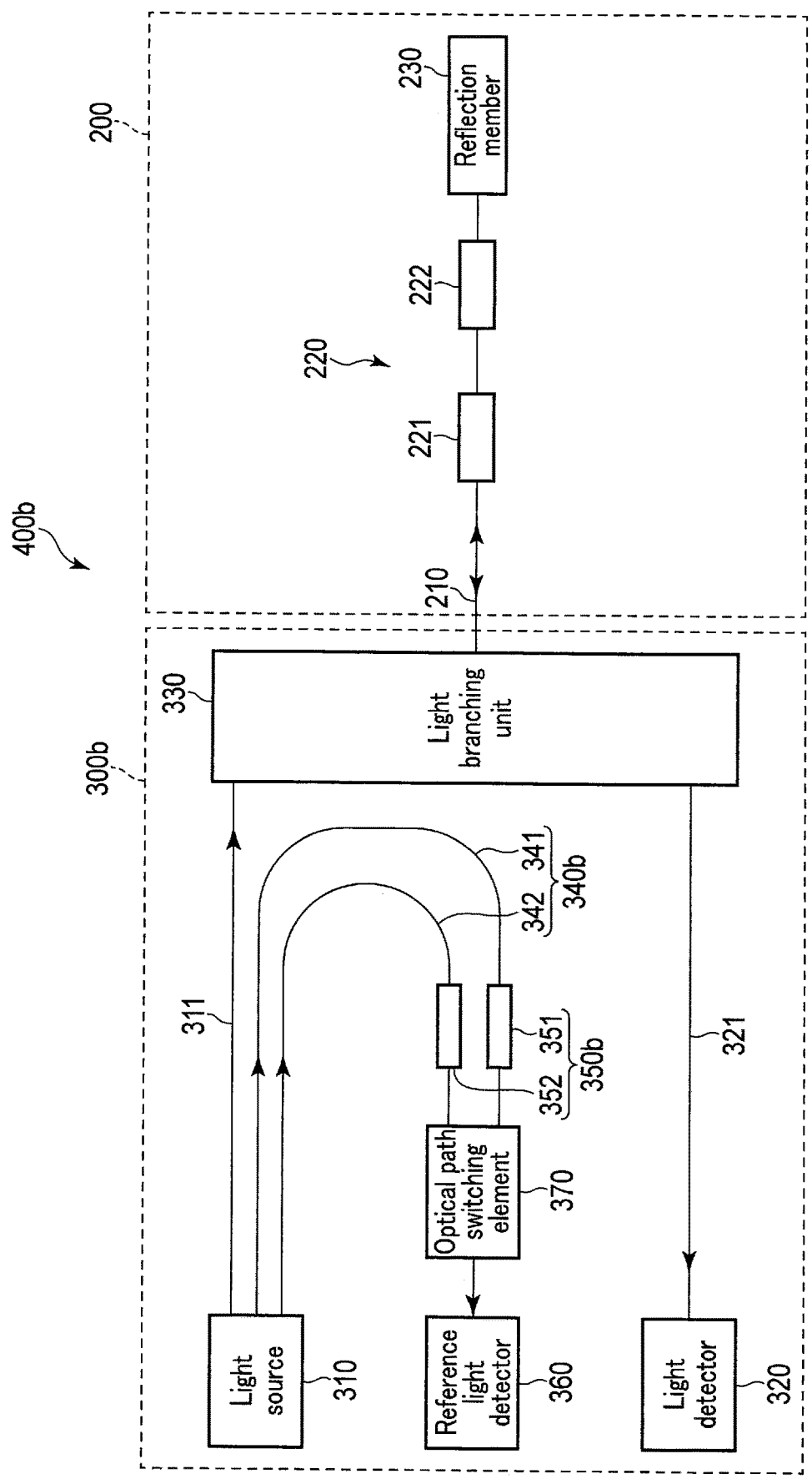
F I G. 15

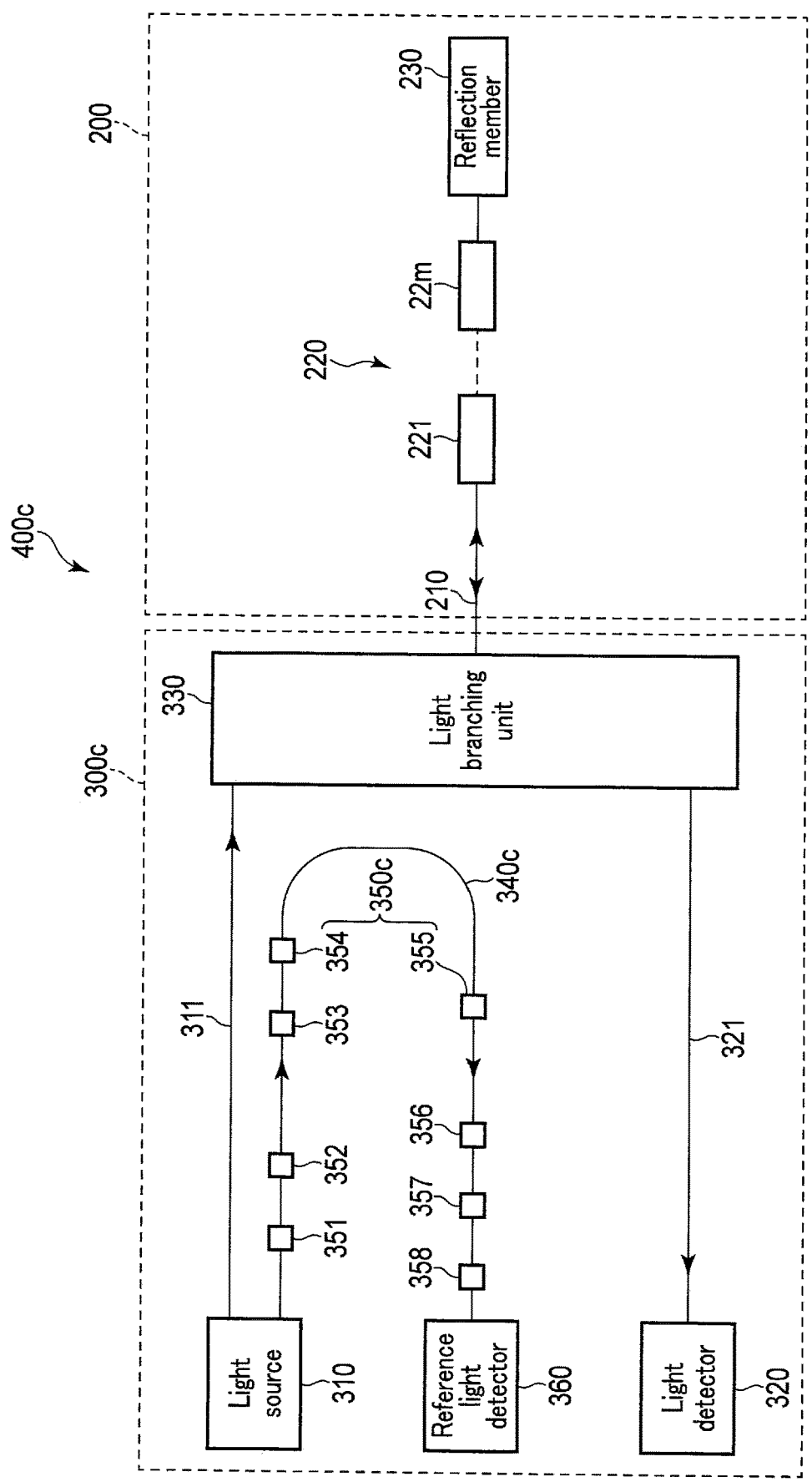
F I G. 16

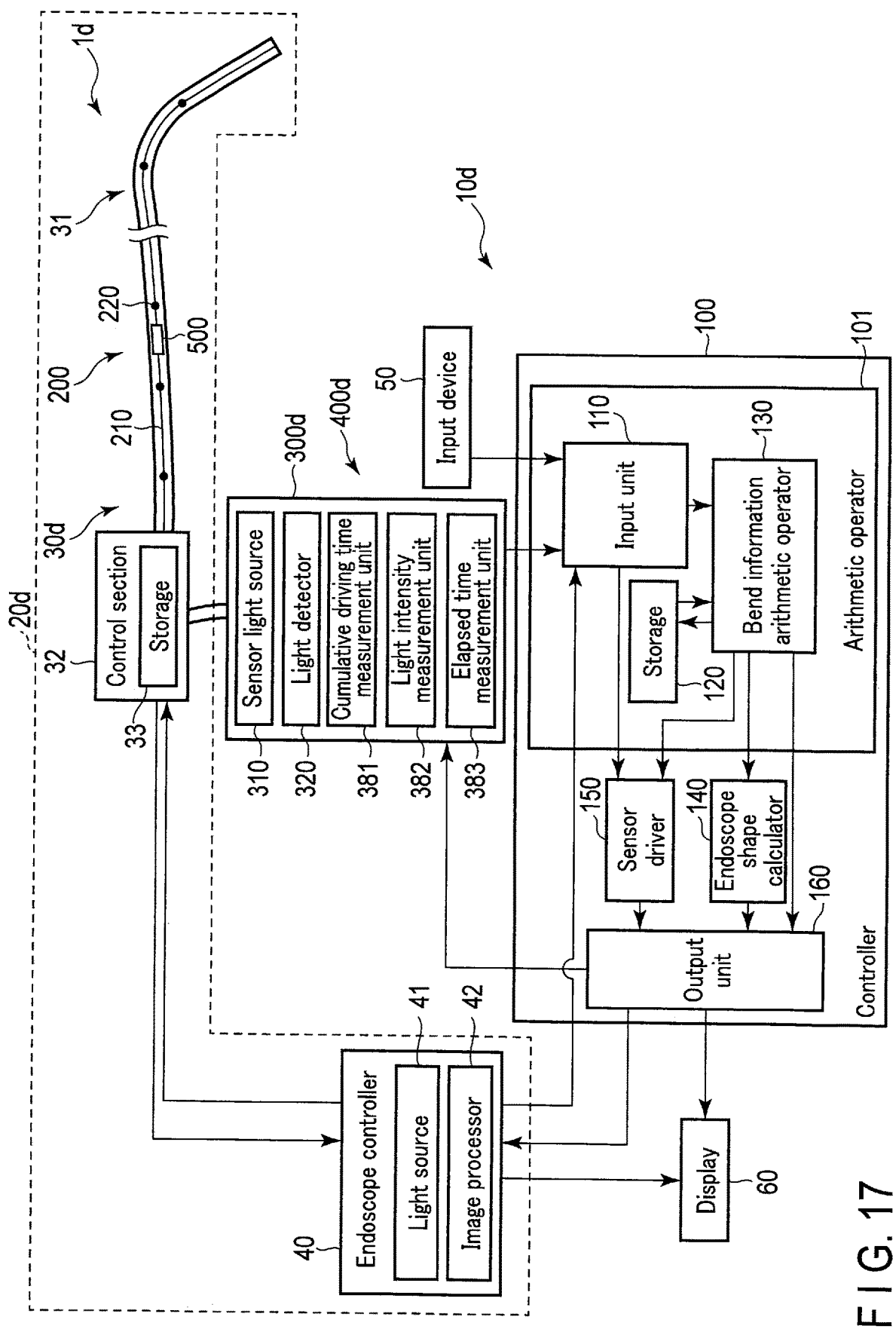
F I G. 17

BEND INFORMATION COMPUTATION APPARATUS, ENDOSCOPE SYSTEM INCLUDING THE APPARATUS, AND BEND INFORMATION COMPUTATION METHOD

CROSS-REFERENCE TO RELATED APPLICATIONS

This application is a Continuation Application of PCT Application No. PCT/JP2016/087944, filed Dec. 20, 2016, the entire contents of which are incorporated herein by reference.

BACKGROUND OF THE INVENTION

1. Field of the Invention

The present invention relates to a bend information computation apparatus configured to compute bend information including a bend direction and a bend magnitude, an endoscope system including the bend information computation apparatus, and a bend information computation method.

2. Description of the Related Art

A bend information computation apparatus that is incorporated into a flexible insertion section of an insertion apparatus, for example, an endoscope, and that detects bend information of the insertion section is known. For example, Japanese Patent No. 4714570 discloses an endoscope shape-detecting probe as a bend information computation apparatus. The probe includes an optical fiber that is incorporated into an insertion section of an endoscope and that bends integrally therewith. The optical fiber is provided with two optical modulators for detecting curvatures in two directions approximately orthogonal to each other at approximately the same positions with respect to a longitudinal direction of the optical fiber. Each optical modulator modulates the intensity and the like of wavelength components of light transmitted through the optical fiber. In this probe, the curvature of the optical fiber at the optical modulators and, in addition, the curvature of the insertion section that is bent integrally with the optical fiber are detected based on changes in the intensities and the like of the wavelength components before and after passing through the optical modulators.

BRIEF SUMMARY OF THE INVENTION

An embodiment of the present invention is a bend information computation apparatus. The bend information computation apparatus includes: an input unit into which detected light quantity information that represents a relation between a wavelength in a predetermined wavelength band and a light quantity is input, the detected light quantity information being acquired by using a sensor including a light guide having at least one light absorber and configured to change a light quantity of light that is transmitted through the light guide according to a bent state of the light absorber to detect a light quantity of the light after a change; and an arithmetic operator configured to compute bend information that represents a bend direction and a bend magnitude of each light absorber based on the detected light quantity information, an absorption spectrum of each light absorber, a bend coefficient of each light absorber that varies according to a bend direction and a bend magnitude of each light absorber, and a unique characteristic value of each light absorber. The unique characteristic value includes a value for a correction relating to the bend coefficient.

Another embodiment of the present invention is an endoscope system. The endoscope system includes: an insertion section incorporated with a light guide having at least one light absorber, configured to change a light quantity of light that is transmitted through the light guide according to a bent state of the light absorber; a sensor configured to detect a light quantity of the light after a change; an input unit into which detected light quantity information that represents a relation between a wavelength in a predetermined wavelength band and a light quantity that is acquired by the sensor is input; and an arithmetic operator configured to compute bend information that represents a bend direction and a bend magnitude of each light absorber based on an absorption spectrum of each light absorber, a bend coefficient of each light absorber that varies according to a bend direction and a bend magnitude of each light absorber, and a unique characteristic value of each light absorber. The unique characteristic value includes a value for a correction relating to the bend coefficient.

Another embodiment of the present invention is a bend information computation method. The bend information computation method includes: acquiring detected light quantity information that represents a relation between a wavelength in a predetermined wavelength band and a light quantity by using a sensor including a light guide having at least one light absorber and configured to change a light quantity of light that is transmitted through the light guide according to a bent state of the light absorber to detect a light quantity of the light after a change; acquiring an absorption spectrum of each light absorber, a bend coefficient of each light absorber that varies according to a bend direction and a bend magnitude of each light absorber, and a unique characteristic value of each light absorber; and computing bend information that represents a bend direction and a bend magnitude of each light absorber based on the detected light quantity information, the absorption spectrum, the bend coefficient, and the unique characteristic value. The unique characteristic value includes a value for a correction relating to the bend coefficient.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view that schematically illustrates an example of an endoscope system including a bend information computation apparatus according to a first embodiment of the present invention.

FIG. 2 is a block diagram illustrating an example of a fiber sensor of a bend information computation apparatus.

FIG. 15 is a view that schematically illustrates an example of a configuration for determining a correction value for correcting changes over time in the absorption spectrum of a light absorber of a detection target.

FIG. 16 is a view that schematically illustrates an example of a configuration for determining a correction value for correcting changes over time in the absorption spectrum of a light absorber that of a detection target.

FIG. 17 is a view that schematically illustrates an example of an endoscope system including a bend information computation apparatus for determining a correction value for correcting changes over time in the absorption spectrum of a light absorber that of a detection target.

DETAILED DESCRIPTION OF THE INVENTION

First Embodiment

Figure 3:
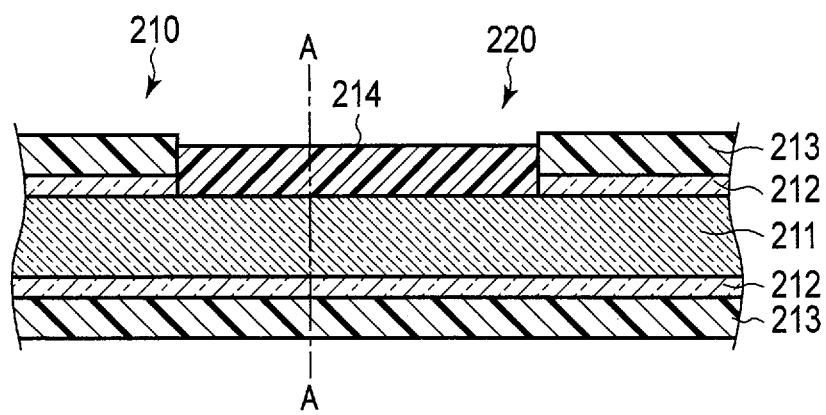
FIG. 3 is a cross-sectional view including an optical axis of a light guide of a sensor.

FIG. 1 is a view that schematically illustrates an example of an endoscope system 1 including a bend information computation apparatus 10 according to a first embodiment of the present invention. The endoscope system 1 includes the bend information computation apparatus 10, an endoscope apparatus 20, an input device 50, and a display 60. The endoscope apparatus 20 includes an endoscope 30 and an endoscope controller 40. The endoscope 30 is connected to the endoscope controller 40 through an unshown universal cord.

The endoscope 30 includes an insertion section 31 to be inserted into an insertion target, and a control section 32 coupled to a proximal end side of the insertion section 31. The insertion section 31 is an elongated tubular portion that is on an endoscope distal-end side, and has flexibility. An illumination optical system, an observation optical system, an imaging element, and the like, which are not illustrated in the drawing, are incorporated into the insertion section 31 at the distal end thereof. The insertion section 31 includes a bendable section that is bent in a desired direction by a user operating the control section 32. Various kinds of operations of the endoscope 30, including the aforementioned bending operation, are input into the control section 32.

The endoscope controller 40 includes a light source 41 for supplying illumination light to the illumination optical system of the endoscope 30. The light source 41 includes a common light emitting device such as a halogen lamp, a xenon lamp, a laser diode (LD), or a light emitting diode (LED). The endoscope controller 40 performs control of various operations of the endoscope 30 and the light source 41, such as controlling driving of the imaging element of the endoscope 30, controlling driving of the light source 41, and controlling adjustment of illumination light from the light source 41. The endoscope controller 40 also includes an image processor 42 for processing images acquired by the observation optical system and imaging element of the endoscope 30.

The bend information computation apparatus 10 is an apparatus for computing bend information with respect to the insertion section 31 of the endoscope 30. In the present description, a bend direction and a bend magnitude are referred to collectively as "bend information". The bend information computation apparatus 10 includes a controller 100 and a fiber sensor 400 that comprises a sensor 200 and a sensor controller 300. These components are described in detail later.

The input device 50 is a general device for input, such as a keyboard or a mouse. The input device 50 is connected to the controller 100 of the bend information computation apparatus 10. The input device 50 is used by a user to input various instructions for operating the bend information computation apparatus 10. Note that, the input device 50 may be a storage medium. In this case, the information stored in the storage medium is input to the controller 100.

The display 60 is a general monitor such as a liquid crystal display. The display 60 is connected to the endoscope controller 40, and displays an observation image acquired by the endoscope 30. The display 60 is also connected to the bend information computation apparatus 10, and displays bend information obtained by the bend information computation apparatus 10 as well as a bent shape of the insertion section 31 and the like.

Next, the fiber sensor 400 of the bend information computation apparatus 10 will be described. FIG. 2 is a block diagram illustrating an example of the fiber sensor 400 that comprises the sensor 200 and the sensor controller 300. The sensor 200 includes a light guide 210, at least one detection target 220 that is provided in the light guide 210, and a reflection member 230. The sensor controller 300 includes a sensor light source 310, a light detector 320, and a light branching unit 330.

The light guide 210 is, for example, an optical fiber, and has flexibility. The proximal end of the light guide 210 is connected to the light branching unit 330 of the sensor controller 300. As schematically illustrated in FIG. 1, the light guide 210 is incorporated into the insertion section 31 of the endoscope 30 along the longitudinal direction of the insertion section 31. At least one detection target 220 of the light guide 210 is arranged at a point where, or across a region where, bend information is to be obtained in the insertion section 31.

FIG. 1 and FIG. 2 illustrate detection targets 220. These detection targets 220 include a first detection target 221, and can further include up to an $m^{th}$ detection target $22m$. That is, "m" detection targets 220 can be provided in the light guide 210. Here, "m" represents an arbitrary number. The m detection targets 221 to $22m$ are arranged at different positions in the longitudinal direction (optical-axis direction) of the light guide 210, that is, are spaced apart from each other.

Figure 4:
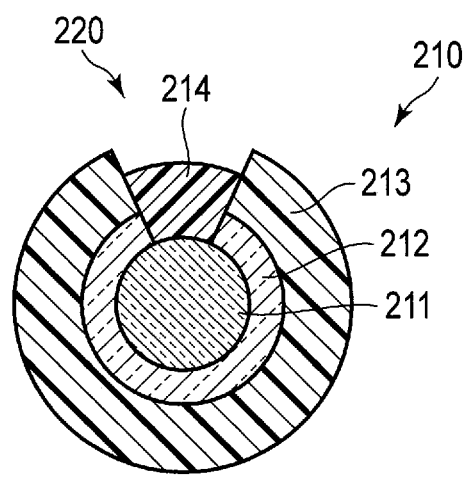
FIG. 4 is a cross-sectional view in a radial direction of the light guide along a line A-A in FIG. 3.

FIG. 3 is a cross-sectional view that includes the optical axis of the light guide 210. FIG. 4 is a cross-sectional view in a radial direction of the light guide, which is a view along a line A-A in FIG. 3. The light guide 210 comprises a three-layer structure that includes a core 211, a cladding 212 surrounding the core 211, and a jacket (covering, buffer) 213 surrounding the cladding 212.

The detection target 220 is formed by removing a part of the jacket 213 and a part of the cladding 212 to expose the core 211, and then providing a light absorber 214 on the exposed core 211. A material that has been colored by means of a coloring material (dye) and whose refractive index is greater than the refractive index of the core 211 and is smaller than the refractive index of the jacket 213 is used as the light absorbent that comprises the light absorber 214. For example, a dye, a colorant, or metallic nanoparticles is used as the coloring material.

The reflection member 230 is connected to the distal end of the light guide 210, that is, to the side to which the light branching unit 330 of the sensor controller 300 is not connected. The reflection member 230 is, for example, a mirror. The reflection member 230 reflects light that has been transmitted to the distal end from the proximal end of the light guide 210 so as to return it in the direction in which the light branching unit 330 is present.

The sensor light source 310 (hereunder, referred to simply as "light source 310") includes, for example, a general light emitting element such as a halogen lamp, a xenon lamp, a laser diode (LD), or a light emitting diode (LED). The light detector 320 is a detector configured to acquire a light intensity for each wavelength (wavelength band), and includes a spectroscope, a combination of a light receiving element and a color filter, or the like. The light branching unit 330 is a branching unit configured to branch light that is transmitted from the light source 310 to the sensor 200 through a light guide 311 and light that is transmitted from the sensor 200 to the light detector 320 through a light guide 321, and includes an optical coupler, a semi-transparent mirror, or the like. The respective light guides 311 and 321 may also be an optical fiber that has flexibility.

The operation of the fiber sensor 400 will now be described. The light source 310 emits light of a predetermined emission wavelength range. The emitted light is guided from the light guide 311 to the light guide 210 through the light branching unit 330, is reflected and returned by the reflection member 230, is guided again to the light guide 321 from the light guide 210 through the light branching unit 330, and reaches the light detector 320. The light detector 320 detects a spectrum of light that has passed through the detection targets 220 (221 to 22m), and has been reflected by the reflection member 230 and returned to the light detector 320, that is, detected light quantity information that represents a relation between a wavelengths in a predetermined wavelength range and a light intensity (light quantity).

Here, a change in the quantity of light absorbed by the light absorber 214 of the detection target 220 that is caused by a change in the bent state of the detection target 220 will be described. The light absorber 214 absorbs light of a predetermined wavelength (wavelength band) among the light transmitted through the light guide 210. For example, in a case where the detection target 220 is in a linear state, a part of light that is guided through the light guide 210 is absorbed by the light absorber 214. In contrast, in a case where the light guide 210 is bent so that the detection target 220 is located on the inner side of the bend, since the quantity of light falling on the light absorber 214 decreases, the quantity of light absorbed by the light absorber 214 is reduced. Accordingly, the light transmission quantity of the light transmitted through the light guide 210 increases in comparison to when the light guide 210 is in a linear state. On the other hand, in a case where the light guide 210 is bent so that the detection target 220 is located on the outer side of the bend, since the quantity of light falling on the light absorber 214 increases, the quantity of light absorbed by the light absorber 214 increases. Accordingly, the light transmission quantity of the light transmitted through the light guide 210 decreases in comparison to when the light guide 210 is in a linear state.

Thus, the detection target 220 modulates the light that is transmitted through the light guide 210 according to the bent state of the detection target 220. In the present embodiment, the light absorber 214 of the detection target 220 modulates the quantity of light (light intensity) that is transmitted through the light guide 210. In other words, since the quantity of light absorbed by the light absorber 214 of the detection target 220 changes according to the bent state of the detection target 220, the quantity of light that is transmitted through the light guide 210 changes. The bend information computation apparatus 10 computes bend information of the detection targets 220, utilizing such changes in light quantity, that is, based on the spectrum detected by the light detector 320, in other words, the detected light quantity information.

Note that, in a case where the detection targets 221 to 22m are provided in the light guide 210, for example, light absorbers 214 having different light absorptivities at respective wavelengths, that is, having different light modulation characteristics, are used for the detection targets 220, respectively. That is, light absorbers 214 of a number of different kinds that is the same as the number of the detection targets 221 to 22m are prepared. In this case, the characteristics (relation between wavelength and quantity of light absorbed) of the absorption spectrum of the respective light absorbers 214 differ for the respective detection targets 221 to 22m.

Next, the controller 100 of the bend information computation apparatus 10 will be described with reference again to FIG. 1. The controller 100 is constituted by an electronic calculator, which is a personal computer, for example. The controller 100 includes an input unit 110, a storage 120, a bend information arithmetic operator 130, an endoscope shape calculator 140, a sensor driver 150, and an output unit 160. Among these components, the input unit 110, the storage 120, and the bend information arithmetic operator 130 constitute an arithmetic operator 101. The controller 100 is communicably connected to the endoscope controller 40. Note that, although the controller 100 of the bend information computation apparatus 10 and the endoscope controller 40 are separate members in the configuration illustrated in FIG. 1, the controller 100 may be incorporated into the endoscope controller 40.

The aforementioned detected light quantity information is input into the input unit 110 from the light detector 320 of the sensor controller 300. The input unit 110 transmits the detected light quantity information to the bend information arithmetic operator 130. Further, information output from the endoscope controller 40 is also input into the input unit 110. Alternatively, information that has been input into the input device 50 is also input into the input unit 110. The input unit 110 transmits signals that include the input information to the bend information arithmetic operator 130 or the sensor driver 150.

The storage 120 stores various kinds of information necessary for arithmetic operations that are executed by the bend information arithmetic operator 130. The storage 120 stores, for example, programs including a calculation algorithm.

The bend information arithmetic operator 130 calculates the bend information of each detection target 220 based on information such as the detected light quantity information acquired through the input unit 110, information stored in the storage 120, a calculation formula, and the like. The bend information arithmetic operator 130 transmits the calculated bend information of each detection target 220 to the endoscope shape calculator 140 and the output unit 160. Further, the bend information arithmetic operator 130 outputs information that relates to the operation of the light detector 320 that is necessary for the bend information calculation, such as a gain of the light detector 320, to the sensor driver 150.

The endoscope shape calculator 140 includes, for example, a CPU or an ASIC. The endoscope shape calculator 140 calculates the shape of the insertion section 31 of the endoscope 30 in which the detection targets 220 are arranged, based on bend information of each detection target 220 that has been calculated by the bend information arithmetic operator 130. The calculated shape of the insertion section 31 is transmitted to the output unit 160. Note that, the endoscope shape calculator 140 may be incorporated into the bend information arithmetic operator 130.

The sensor driver 150 generates a driving signal for the light detector 320 based on information acquired from the input unit 110 or the bend information arithmetic operator 130. By means of the driving signal, the sensor driver 150, for example, switches the light detector 320 on or off based on a user instruction input into the input device 50 that has been acquired through the input unit 110, or adjusts the gain of the light detector 320 based on information acquired from the bend information arithmetic operator 130. The sensor driver 150 also controls operation of the light source 310. The sensor driver 150 transmits the generated driving signal to the output unit 160.

The output unit 160 outputs bend information of the detection targets 220 that has been acquired from the bend information arithmetic operator 130 or the shape of the insertion section 31 that has been acquired from the endoscope shape calculator 140 to the display 60. The output unit 160 also outputs bend information of the detection targets 220 that has been acquired from the bend information arithmetic operator 130 or the shape of the insertion section 31 that has been acquired from the endoscope shape calculator 140 to the endoscope controller 40. Further, the output unit 160 outputs the driving signal from the sensor driver 150 to the light detector 320.

Next, operation of the endoscope system 1 and the bend information computation apparatus 10 of the present embodiment will be described.

The insertion section 31 of the endoscope 30 is inserted into an insertion target by the user. During insertion, the insertion section 31 bends to follow the bent state of the insertion target. The endoscope 30 obtains an image signal by means of the observation optical system and the imaging element that are provided in the distal end of the insertion section 31. The obtained image signal is transmitted to the endoscope controller 40. The endoscope controller 40 creates an observation image at the image processor 42 based on the acquire image signal, and causes the display 60 to display the created observation image.

When the user wishes to cause the display 60 to display bend information of the insertion section 31 of the endoscope 30, or when the user wishes to cause the endoscope controller 40 to perform various operations using the bend information of the insertion section 31, the user inputs the corresponding instruction to the controller 100 through the input device 50. The bend information computation apparatus 10 then operates.

When the bend information computation apparatus 10 operates, the light source 310 of the sensor controller 300 is activated based on a driving signal that is transmitted to the sensor driver 150, the output unit 160, and the sensor controller 300. The light source 310 emits light of a predetermined emission wavelength range. Then, as described above, the quantity of light that is transmitted through the light guide 210, which is the intensity of the light that is changed in accordance with the bent state of the detection target(s) 220, is detected for each wavelength by the light detector 320. That is, the light detector 320 acquires detected light quantity information.

The light detector 320 transmits the acquired detected light quantity information to the input unit 110 of the controller 100. The transmitted detected light quantity information is acquired by the bend information arithmetic operator 130, so that the bend information arithmetic operator 130 calculates bend information of the respective detection targets 220.

The bend information of the respective detection targets 220 that has been calculated by the bend information arithmetic operator 130 is acquired by the endoscope shape calculator 140. The endoscope shape calculator 140 calculates the shape of the insertion section 31 of the endoscope 30 based on the bend information of the respective detection targets 220.

The bend information of the respective detection targets 220 that has been calculated by the bend information arithmetic operator 130 or the shape of the insertion section 31 that has been calculated by the endoscope shape calculator 140 is acquired by the endoscope controller 40 through the output unit 160. The endoscope controller 40 controls the operation of the endoscope 30 based on the bend information of the respective detection targets 220 or the shape of the insertion section 31.

Further, the bend information of the respective detection targets 220 that has been calculated by the bend information arithmetic operator 130 or the shape of the insertion section 31 that has been calculated by the endoscope shape calculator 140 is displayed on the display 60 through the output unit 160.

In addition, the information input into the input unit 110 and the bend information of the respective detection targets 220 calculated by the bend information arithmetic operator 130 are acquired by the sensor driver 150. Based on the acquired information, the sensor driver 150 transmits a driving signal to the light detector 320 through the output unit 160, to thereby control the operation of the light detector 320.

Thus, in the bend information computation apparatus 10, bend information of the respective detection targets 220 is computed by the bend information arithmetic operator 130. Based on the computed bend information of the respective detection targets 220, the endoscope shape calculator 140 calculates the shape of the insertion section 31 of the endoscope 30. Thus, the user can obtain bend information of each detection target 220 or the shape of the insertion section 31 while operating the endoscope 30. In addition, the endoscope controller 40 can appropriately control the operation of the endoscope 30 in accordance with the calculated bend information of each detection target 220 or the shape of the insertion section 31.

Figure 5:
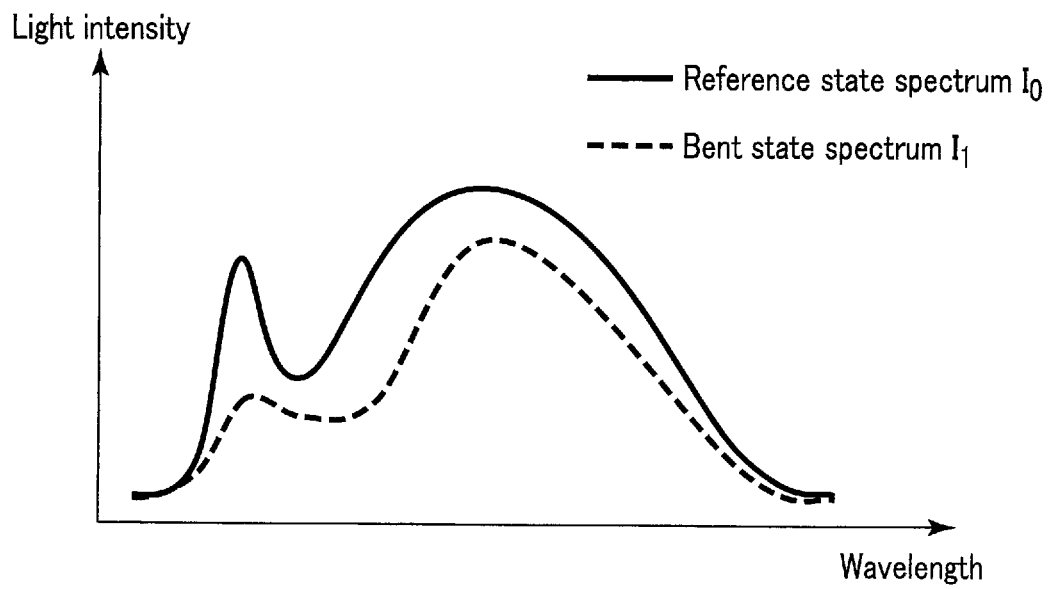
FIG. 5 is a view illustrating an example of relations between wavelengths and light intensities in a reference state and a bent state.

Next, an outline of the manner in which bend information of each detection target 220 is computed by the bend information arithmetic operator 130 will be described A spectrum that is the relation between wavelengths and light intensities detected by the light detector 320 when the respective detection targets 220 are in a predetermined shape that serves as a reference is referred to as "reference state spectrum $I_0$". The term "reference state" refers to, for example, a time when the detection targets 220 are in a linear state, that is, a state in which the area of the light guide 210 that includes the detection targets 220, is in a linear state. Naturally, a state other than the aforementioned state may be adopted as the reference state. An example of the reference state spectrum $I_0$ is shown by a solid line in FIG. 5.

The reference state spectrum $I_0$, for example, has been acquired in advance at the time of factory shipment of the bend information computation apparatus 10, and is stored in the storage 120. Alternatively, the reference state spectrum $I_0$ may be stored in advance in an unshown sensor storage that is provided in the sensor 200 or the sensor controller 300. Alternatively, the reference state spectrum $I_0$ may be acquired each time detachment and reconnection of the light branching unit 330 of the sensor controller 300 and the light guide 210 of the sensor 200 is performed at the time of maintenance by service personnel or the like.

In a state in which the detection targets 220 are bent, as described above, since the quantity of light absorbed by the light absorber 214 of each detection target 220 changes according to the bend direction and bend magnitude of the relevant detection target 220, a spectrum that is the relation between wavelengths and light intensities detected by the light detector 320, that is, a bent state spectrum $I_1$, is different from the reference state spectrum $I_0$. An example of the bent state spectrum $I_1$ is shown by a dashed line in FIG. 5.

Figure 6:
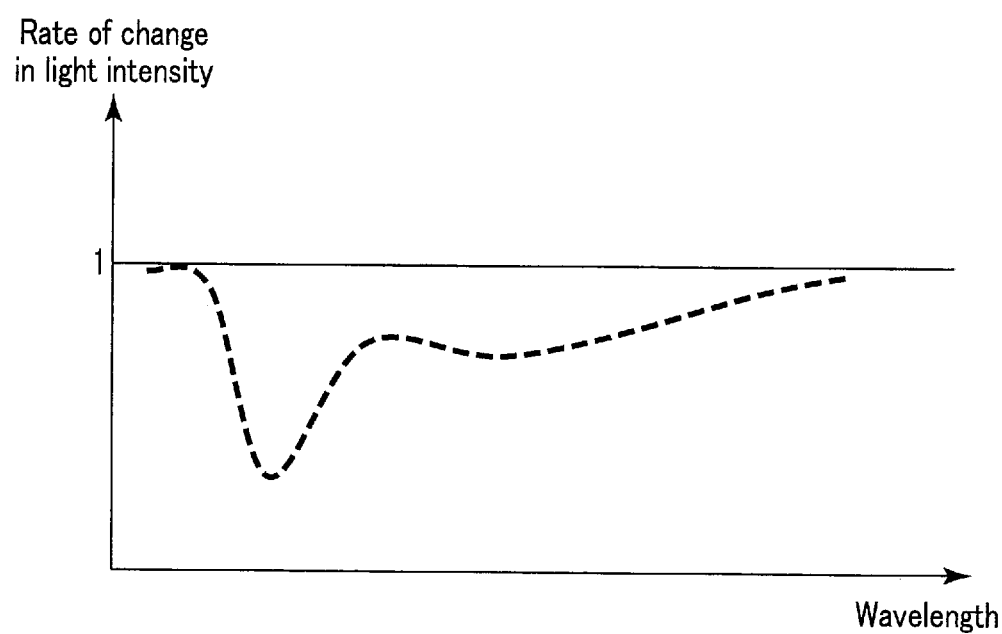
FIG. 6 is a view illustrating an example of a relation between a wavelength and a rate of change in light intensity.

The bend information arithmetic operator 130 of the bend information computation apparatus 10, for example, as illustrated in FIG. 6, determines bend information (a bend direction and a bend magnitude) of each detection target 220 based on a rate of change $I_1/I_0$ that is a ratio between the reference state spectrum $I_0$ and the bent state spectrum $I_1$. The rate of change $I_1/I_0$ illustrated in FIG. 6 is a change in the spectrum that is caused by bending of the detection targets 220.

Next, a phenomenon that can occur due to individual differences or variations between absorption spectra of the light absorbers 214 provided in the detection targets 220 will be described with reference to FIG. 7 to FIG. 9.

As described above, at the respective detection targets 220, which are optical modulators, the spectrum (light quantity with respect to each wavelength) changes according to the bent state of the respective detection targets 220. The spectrum of the light absorber 214 provided in each detection target 220 is acquired by bending the relevant detection target 220. In a case where, as in a configuration (I) of the light guide 210 illustrated in FIG. 7, the first detection target 221 and a second detection target 222 are provided in the light guide 210, the spectrum of a first light absorber 215 is acquired with the first detection target 221 including the first light absorber 215 being kept in a linear shape, and only the second detection target 222 including a second light absorber 216 being bent, that is, only one detection target being bent.

Figure 8:
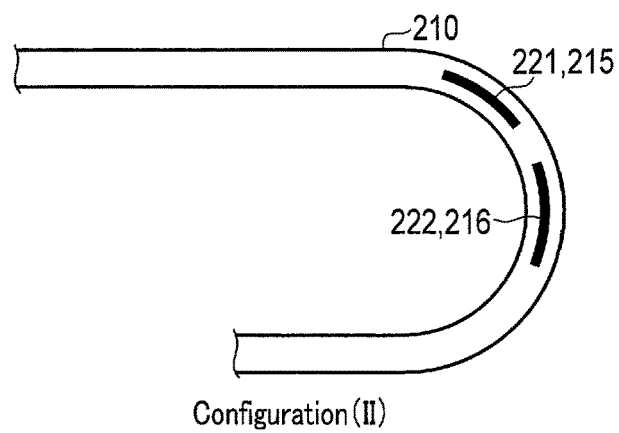
FIG. 8 is a view illustrating a bent state of a light guide having a configuration (II).

However, in a case where the first detection target 221 and the second detection target 222 that are adjacent constitute a detection target group as in a configuration (II) of the light guide 210 illustrated in FIG. 8, it is not possible to bend only one detection target because when one of the detection targets 221 (or 222) is bent, the other detection target 222 (or 221) also inevitably bends. Therefore, in the case of configuration (II), the spectrum of the light absorber 215 or 216 of the detection target 221 or 222 is acquired not from the detection target 221 or 222 itself, but by means of a substitute detection target that is equivalent to the detection target 221 or 222, or by other optical property acquisition means that simulates absorption of light by the light absorber 215 or 216 of the detection target 221 or 222. For example, a spectrum of a liquid solution/liquid dispersion is acquired by dissolving or dispersing the coloring material constituting the light absorber 215 or 216 in a liquid.

Figure 7:
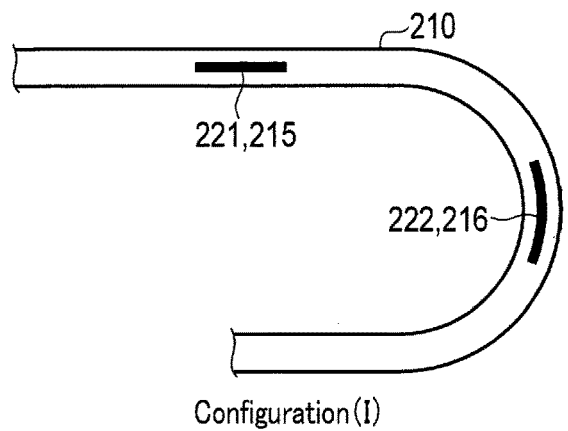
FIG. 7 is a view illustrating a bent state of a light guide having a configuration (I).
Figure 9:
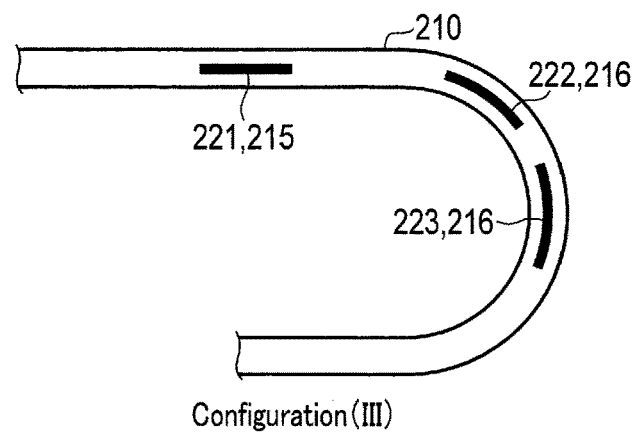
FIG. 9 is a view illustrating a bent state of a light guide having a configuration (III).

Note that, although in the configuration (I) of the light guide 210 shown in FIG. 7 and the configuration (II) of the light guide 210 shown in FIG. 8, although the first light absorber 215 provided in the first detection target 221 and the second light absorber 216 provided in the second detection target 222 are different light absorbers, in a configuration (III) of the light guide 210 shown in FIG. 9, among detection targets 221, 222, and 223, identical light absorbers 216 are provided in the second detection target 222 and a third detection target 223 that are adjacent. In other words, a detection target in which the same light absorber 216 is provided is split into two and arranged in the light guide 210. According to this configuration, the detection range by the light absorber 216 is lengthened, the structural strength of the light guide 210 is maintained, or alternatively, a fixing location for fixing the light guide 210 to another member is secured between the second detection target 222 and the third detection target 223 (that is, the light guide 210 is not fixed at a location at which a detection target is present).

In a case where identical light absorbers 216 are provided in the second detection target 222 and the third detection target 223 that are bent, as in the configuration (III) of the light guide 210 shown in FIG. 9, these two detection targets 222 and 223 are regarded as a single detection target. That is, the configuration (III) is treated in the same manner as the configuration (I), and the two detection targets 222 and 223 in which the identical light absorbers 216 are arranged are set to the same bent state (curvature). The number of detection targets that are regarded as a single detection target may also be three or more.

For example, in order to acquire the spectrums of the respective light absorbers of the detection targets 221 and 222 constituting a detection target group in the light guide 210 with the configuration (II), a light guide 210 with the configuration (I) is separately prepared as an alternative detection target. The spectrums of the respective light absorbers of the detection targets 221 and 222 are then acquired with each of the detection targets 221 and 222 with being individually bent in the manner described above with regard to the configuration (I).

Identical first light absorbers 215 and second light absorbers 216 are used in the first detection target 221 and the second detection target 222 of the configurations (I) and (II), respectively. However, the absorption spectrums of the light absorbers 215 and 216 of the detection targets 221 and 222 in the configuration (I) do not completely (strictly) match the absorption spectrums of the light absorbers 215 and 216 of the detection targets 221 and 222 in the configuration (II). The causes for this may be broadly divided into two cases, namely, a case where the absorption spectrum of the coloring material included in the light absorbent constituting the light absorber in each detection target changes (case 1), and a case where the absorption spectrum of the light absorbent changes due to the involvement of absorption of new light (scattering) (case 2).

In case 1, since the absorption spectrum of the light absorber is determined by the dimensions of the coloring material particles, the absorption spectrum will change if there are variations in the dimensions of particles of a coloring material that utilizes plasmon absorption, for example, metallic nanoparticles.

Figure 10:
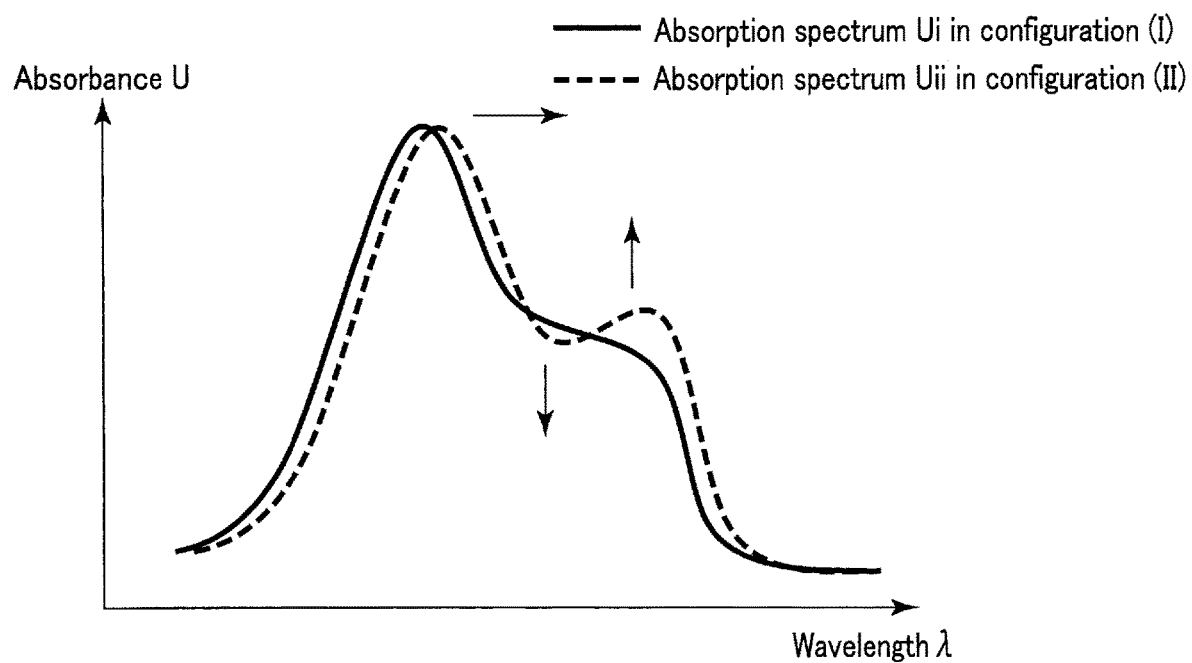
FIG. 10 is a view illustrating an example of relations between wavelengths and absorbance in a case 1.

FIG. 10 is a view that illustrates an example of the relation between a wavelength and absorbance in case 1. An absorption spectrum Ui for the configuration (I) is represented by a solid line, and an absorption spectrum Uii for the configuration (II) is represented by a dashed line. Note that, since the maximal values of the absorbances are normalized, the maximal values of the absorption spectrums Ui and Uii are the same. When the absorption spectrum Ui and the absorption spectrum Uii are compared, it is found that, for example, the peak wavelength of the absorption spectrum Uii is shifted to the long wavelength side relative to the absorption spectrum Ui (a change indicated by an arrow in the right direction in FIG. 10). Further, for example, a peak of the absorption spectrum Uii is changed relative to a peak of the absorption spectrum Ui (a change indicated by an arrow in the vertical direction in FIG. 10).

In case 2, scattering of light occurs due to a coloring material that is dissolved or dispersed in the light absorbent precipitating or aggregating together, and absorption of light occurs in all the wavelength bands and consequently the absorption spectrum changes (a turbid state). For example, dissolution and precipitation occurs in the case of a dye, while dispersion and aggregation occur in the case of a colorant. Further, scattering of light occurs due to contaminants such as impurities that are contained in the light absorbent, dirt that that gets mixed when performing work operations, or the like, and absorption of light occurs in all the wavelength bands and consequently the absorption spectrum changes (a turbid state).

Figure 11:
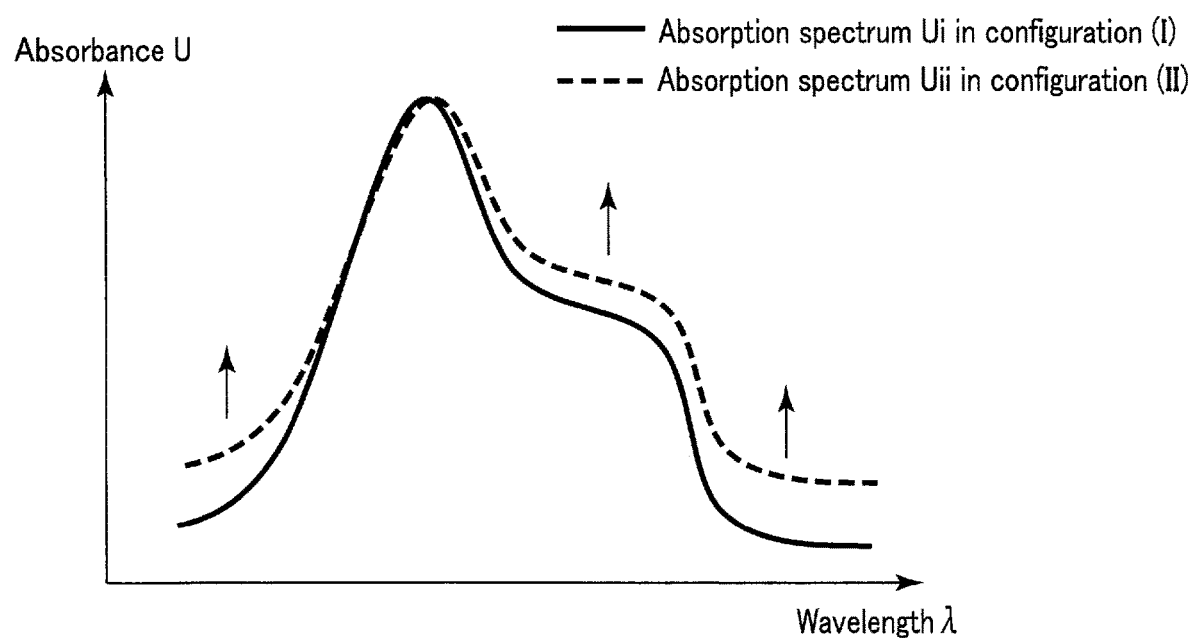
FIG. 11 is a view illustrating an example of relations between wavelengths and absorbance in a case 2.

FIG. 11 is a view that illustrates an example of the relation between a wavelength and absorbance in case 2. An absorption spectrum Ui for the configuration (I) is represented by a solid line, and an absorption spectrum Uii for the configuration (II) is represented by a dashed line. When the absorption spectrum Ui and the absorption spectrum Uii are compared, it is found that, for example, the absorption spectrum Uii is completely shifted upward relative to the absorption spectrum Ui (change indicated by arrows in the upward direction in FIG. 11). That is, absorption of light occurs in an overall manner.

Thus, when light absorbers constituting the detection targets have individual differences, variations, or the like in the absorption spectrums, correct bend information may not be computed by the bend information computation apparatus 10 that includes the light guide 210 with the configuration (II).

As a measure to deal with this phenomenon, in the present embodiment, firstly, a rate of change V of the light quantity with respect to each wavelength is represented by an equation that includes the absorption spectrums of the light absorbers constituting the detection targets as well as bend information. Further, in order to correct individual differences or variations between absorption spectrums of the light absorbers, a correction value that is a unique characteristic value for each detection target is applied to the aforementioned equation.

Before describing the correction of individual differences or variations of the absorption spectrums of the light absorbers, the computation of bend information of detection targets will first be described for a case where correction is not required, that is, the case of the configuration (I). In a case where absorption spectrums of the light absorbers 214 (215, 216) of each detection target 220 (221, 222) can be acquired as in the configuration (I) (including a case where an absorption spectrum of a light absorber of a detection target 220 according to the configuration (II) is completely equal to the configuration (I)), a light-quantity-rate-of-change V of light modulated at the detection targets 220 is represented by a ratio between the reference state spectrum $I_0$ and the bent state spectrum $I_1$ as described above. That is, the light-quantity-rate-of-change V is defined by the following equation (1).

$$V = \frac{I_1}{I_0} \qquad \text{Equation (1)}$$

Further, the light-quantity-rate-of-change V can be expressed using a bend coefficient as shown in the following equation (2)

$$V = V_A \times V_B \qquad \text{Equation (2)}$$
$$= \alpha_A^{U_A} \times \alpha_B^{U_B}$$
$$= \exp(\beta_A U_A + \beta_B U_B)$$

Here, V represents the light-quantity-rate-of-change of the overall fiber sensor 400, which exists for each wavelength in a predetermined wavelength band of light that is emitted from the light source 310 ($V\lambda 1$ to $V\lambda n$). Further, $V_A$ represents the light-quantity-rate-of-change at the first detection target 221, and $V_B$ represents the light-quantity-rate-of-change at the second detection target 222. These light-quantity-rate-of-changes $V_A$ and $V_B$ also exist for each wavelength in a predetermined wavelength band of light that is emitted from the light source 310 ($V_A\lambda 1$ to $V_A\lambda n$, $V_B\lambda 1$ to $V_B\lambda n$). $\alpha_A$ represents a bend coefficient of the first detection target 221, which is a function of curvature and bend direction. Further, $\alpha_B$ represents a bend coefficient of the second detection target 222, which is a function of curvature and bend direction. These bend coefficients $\alpha_A$ and $\alpha_B$ do not depend on the wavelength, and change depending on the bend direction and bend magnitude of each detection target. $U_A$ represents the absorption spectrum of the first light absorber 215 of the first detection target 221, and $U_B$ represents the absorption spectrum of the second light absorber 216 of the second detection target 222. These absorption spectrums $U_A$ and $U_B$ exist for each wavelength in a predetermined wavelength band of light that is emitted from the light source 310 ($U_A\lambda 1$ to $U_A\lambda n$, $U_B\lambda 1$ to $U_B\lambda n$). $\beta_A$ represents a bend coefficient of the first detection target 221, which is a function of curvature and bend direction. $\beta_B$ is a bend coefficient of the second detection target 222, which is a function of curvature and bend direction. These bend coefficients $\beta_A$ and $\beta_B$ do not depend on the wavelength, and change depending on the bend direction and bend magnitude of each detection target.

Accordingly, the bend information arithmetic operator 130 of the bend information computation apparatus 10, for example, acquires the bend coefficients of the first detection target 221 and the second detection target 222 and the absorption spectrum of the first light absorber 215 of the first detection target 221 and the absorption spectrum of the second light absorber 216 of the second detection target 222 from the storage 120 in which each of these coefficients and spectrums are stored in advance, and also acquires detected light quantity information that has been detected by the light detector 320, and can compute the bend information of the detection targets 221 and 222 based on equation (2) that represents a function among these absorption spectrums, the bend coefficients, and the detected light quantity information.

However, as described above, if a change in the absorption spectrum of the light absorber of the respective detection targets occurs as in case 1 (FIG. 10) or case 2 (FIG. 11), bend information cannot be correctly computed based on equation (2).

Hereunder, with respect to the configuration (II), a correction value will be described for a case where the absorption spectrum of a coloring material included in a light absorber changes as in the aforementioned case 1.

For example, if the absorption spectrum of a coloring material included in the light absorbent changes, equation (2) no longer holds. Therefore, in order to compensate for a change in the absorption spectrum, a correction value is applied to the absorption spectrum of the coloring material of the respective light absorbers of the detection targets in the manner shown in equation (3). The correction value is a unique characteristic value for each detection target.

$$V' = V'_A \times V'_B \qquad \text{Equation (3)}$$
$$= \alpha_A^{(U_A+U_{C1})} \times \alpha_B^{(U_B+U_{C2})}$$
$$= \exp\{\beta_A(U_A + U_{C1}) + \beta_B(U_B + U_{C2})\}$$

Figure 12:
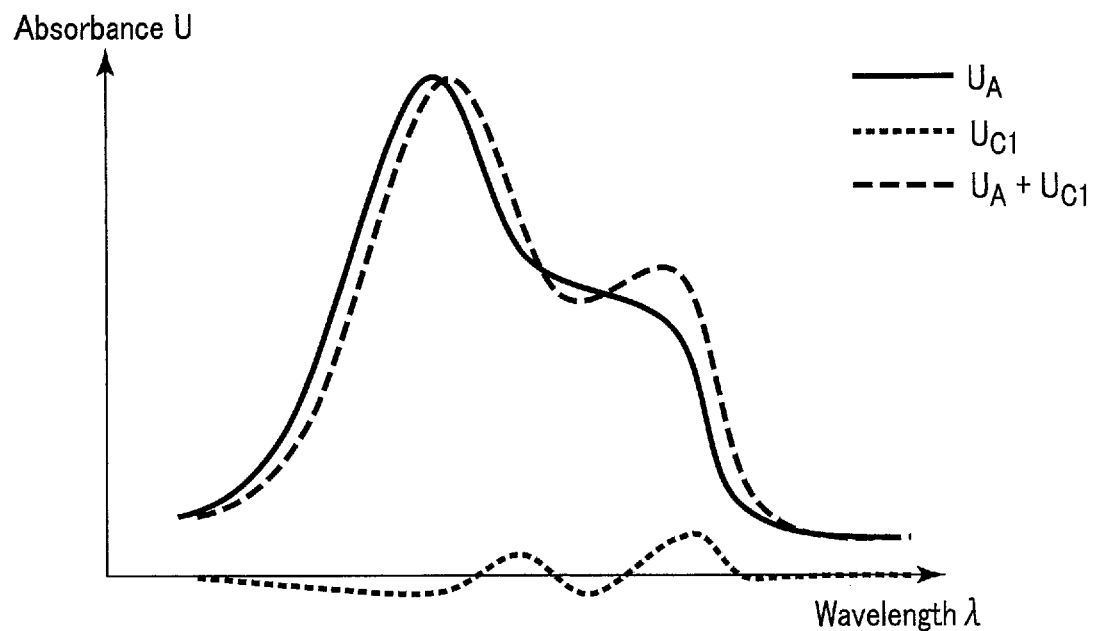
FIG. 12 is a view illustrating an example of relations between wavelengths and absorbance that includes a correction value in a case 1.

Here, $U_{C1}$ represents the correction value of the absorption spectrum of the light absorber 215 of the first detection target 221, and $U_{C2}$ represents the correction value of the absorption spectrum of the light absorber 216 of the second detection target 222. These correction values $U_{C1}$ and $U_{C2}$ of the absorption spectrums exist for each wavelength in a predetermined wavelength band of light emitted from the light source 310 ($U_{c1}\lambda 1$ to $U_{c1}\lambda n$, $U_{c2}\lambda 1$ to $U_{c2}\lambda 2$). In FIG. 12, an example is illustrated of the absorption spectrum $U_A$ of the light absorber 215 of the first detection target 221, the correction value $U_{C1}$ of the absorption spectrum of the light absorber 215 of the first detection target 221, and the sum $U_A+U_{C1}$ that is obtained by adding together the aforementioned $U_A$ and $U_{C1}$.

The correction values $U_{C1}$ and $U_{C2}$ for the absorption spectrums of the respective light absorbers 215 and 216 in the respective detection targets 221 and 222 are determined together with the bend coefficients $\alpha_A$ and $\alpha_B$ so that the total sum of absolute values of the difference between the light-quantity-rate-of-change V defined by equation (1) and a light-quantity-rate-of-change V' determined from equation (3) becomes a minimal value ($\alpha_A$ and $\alpha_B$ are represented by a function of curvature and bend direction as described above) when the detection targets are bent into various shapes, for example.

Note that, in a case where the number of detection targets (kinds of coloring material) increases, correction values that correspond to each of the respective coloring materials are applied.

Accordingly, in the present embodiment, using the fiber sensor 400, the bend information computation apparatus 10 acquires detected light quantity information that represents the relation between wavelengths and light quantities in a predetermined wavelength band of light emitted from the light source 310, by the light detector 320. Note that, the fiber sensor 400 includes the light guide 210 having at least one detection target 220, and the detection target 220 changes the quantity of light that is transmitted through the light guide 210 according to the bent state of the detection target 220. The arithmetic operator 101 of the controller 100 of the bend information computation apparatus 10 acquires the detected light quantity information that has been acquired using the light detector 320. Further, the arithmetic operator 101 acquires, for example, a bend coefficient of the detection target 220, the absorption spectrum of the light absorber 214 of the detection target 220, and a correction value for the absorption spectrum of the light absorber 214 of the detection target 220. The arithmetic operator 101 can compute bend information of the detection target 220 based on equation (3) that represents the relation among the detected light quantity information, the absorption spectrum, the bend coefficient, and the correction value that are acquired.

According to the present embodiment, a correction value is applied to a calculation formula for a light-quantity-rate-of-change that is used in arithmetic operations regarding bend information by the arithmetic operator 101 (the input unit 110, the storage 120, and the bend information arithmetic operator 130), so that, even if the absorption spectrum of the coloring material changes, the light-quantity-rate-of-change of a detection target can be expressed by a bend coefficient equation. Accordingly, a bend information computation apparatus that can perform correct bend information computations even in a case where changes occur in an absorption spectrum can be provided.

Second Embodiment

Hereunder, a correction term that is a unique characteristic value for each detection target that is applied to the aforementioned equation (2) in a case where, in the configuration (II), absorption of new light occurs as in the aforementioned case 2 will be described.

Figure 13:
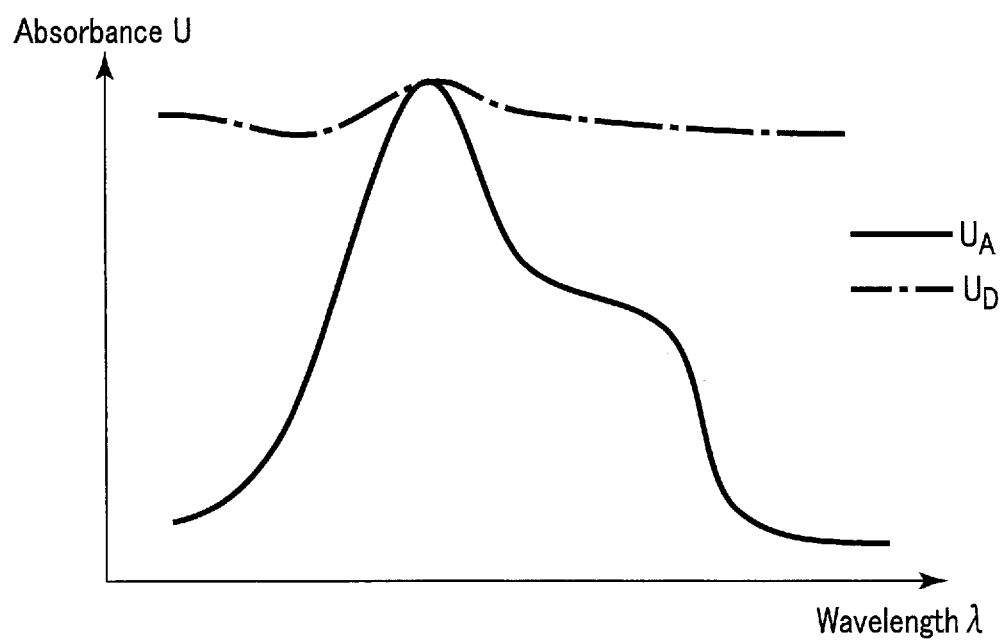
FIG. 13 is a view illustrating an example of relations between wavelengths and absorbance that includes a correction term in a case 2.

In a case where absorption of new light occurs, the aforementioned equation (2) does not hold. Therefore, absorption of new light is regarded as light absorption by a new coloring material, and a correction term that represents a pseudo virtual detection target is applied (FIG. 13).

$$V' = V_A \times V_B \times V_D \qquad \text{Equation (4)}$$
$$= \alpha_A^{U_A} \times \alpha_B^{U_B} \times \alpha_D^{U_D}$$
$$= \exp(\beta_A U_A + \beta_B U_B + \beta_D U_D)$$

Here, $V_D$ represents a light-quantity-rate-of-change at a virtual detection target, which exists for each wavelength in a predetermined wavelength band of light emitted from the light source 310 ($V_D\lambda 1$ to $V_D\lambda n$). $\alpha_D$ represents a bend coefficient of the virtual detection target, which is a function of curvature and bend direction. This bend coefficient does not depend on the wavelength, and changes depending on the bend direction and bend magnitude of the virtual detection target. $U_D$ represents the absorption spectrum of a light absorber at the virtual detection target, which exists for each wavelength in the predetermined wavelength band of light emitted from the light source 310 ($U_D\lambda 1$ to $U_D\lambda n$). $\beta_D$ represents a bend coefficient of the virtual detection target, which is a function of curvature and bend direction. This bend coefficient does not depend on the wavelength, and changes depending on the bend direction and bend magnitude of the virtual detection target. In FIG. 13, an example of an absorption spectrum $U_A$ of the light absorber 215 of the first detection target 221 and an absorption spectrum $U_D$ of the light absorber of the virtual detection target is illustrated.

A correction term in the present embodiment is determined by the same manner as the manner for determining the correction value in the first embodiment. If the number of detection targets increases, correction terms that correspond to each of the detection targets, respectively, are applied.

According to the present embodiment, by the bend information arithmetic operator 130 applying a correction term that represents a pseudo virtual detection target to a light-quantity-rate-of-change that is used in arithmetic operations to bend information, even if absorption of new light occurs at a light absorber, the light-quantity-rate-of-change of a detection target can be expressed by a bend coefficient equation. Accordingly, a bend information computation apparatus that can perform correct bend information computations even in a case where absorption of new light occurs can be provided.

Third Embodiment

Hereunder, a correction value and a correction term that are unique characteristic values for each detection target that are to be applied to the aforementioned equation (2) in a case where, in the configuration (II), both of the aforementioned case 1 and case 2 occur will be described.

According to the present embodiment, by combining the first embodiment and the second embodiment, a correction value and a correction term are applied as shown in equation (5).

$$V' = V'_A \times V'_B \times V_D \quad\quad \text{Equation (5)}$$
$$= \alpha_A^{(U_A+U_{C1})} \times \alpha_B^{(U_B+U_{C2})} \times \alpha_D^{U_D}$$
$$= \exp\{\beta_A(U_A + U_{C1}) + \beta_B(U_B + U_{C2}) + \beta_D U_D\}$$

The correction value and the correction term can be determined by the same manners as those used in the first embodiment and second embodiment. If the number of detection target groups increases, it suffices to apply correction values that correspond to each of the coloring materials, respectively, and correction terms that correspond to each of the detection target groups, respectively.

In the present embodiment also, by applying a correction value and a correction term, even if a change in the absorption spectrum of a coloring material or absorption of new light occurs, a light-quantity-rate-of-change of a detection target group can be expressed by a bend coefficient equation, and thus a bend information computation apparatus that correctly determines a bent state can be provided.

The bend information estimation apparatuses according to the first to third embodiments that are described above can accurately compute bend information of detection targets even when the light absorbers have individual differences or variations in the absorption spectrums, by expressing the rates of change in light quantities at respective wavelengths using a relational equation between absorption spectrums of light absorbers constituting the detection targets and bend information, and applying at least one of a correction value and a correction term (unique characteristic value with respect to each detection target) for correcting individual differences or variations in the absorption spectrums of the light absorbers to the relational equation.

Note that, in the first to third embodiments, the controller 100 may be configured so that, in a case where at least one of a correction value and a correction term exceeds a setting range, the controller 100 notifies the user audibly or visually to that effect by notification of an error code or notification of the fact that the computing accuracy has decreased.

Fourth Embodiment

According to the fourth embodiment, in a case where the absorption spectrum of the light absorber 215 of the detection target 220 changes over time due to light energy, oxidization, or heat that is applied to the detection target 220 of the light guide 210, a correction value is applied to the light-quantity-rate-of-change.

In a case where the absorption spectrum of the light absorber 215 changes over time due to light energy, oxidization, or heat that is applied to the detection target 220, a correction value that is a unique characteristic value for each detection target is applied as shown in the following equation (6).

$$V' = V'_A \times V'_B \quad\quad \text{Equation (6)}$$
$$= \alpha_A^{(U_A+U_{C1}+U_{P1}+U_{O1}+U_{T1})} \times \alpha_B^{(U_B+U_{C2}+U_{P2}+U_{O2}+U_{T2})}$$
$$= \exp\{\beta_A(U_A + U_{C1} + U_{P1} + U_{O1} + U_{T1}) +$$
$$\beta_B(U_B + U_{C2} + U_{P2} + U_{O2} + U_{T2})\}$$

Here, $U_{P1}$ represents a value for correcting a change due to light energy in the absorption spectrum of the first light absorber 215 of the first detection target 221. $U_{O1}$ represents a value for correcting a change due to oxidization in the absorption spectrum of the first light absorber 215 of the first detection target 221. $U_{T1}$ represents a value for correcting a change due to heat in the absorption spectrum of the first light absorber 215 of the first detection target 221. These correction values $U_{P1}$, $U_{O1}$, and $U_{T1}$ exist for each wavelength in a predetermined wavelength band of light emitted from the light source 310 ($U_{P1}\lambda 1$ to $U_{P1}\lambda n$, $U_{O1}\lambda 1$ to $U_{O1}\lambda n$, $U_{T1}\lambda 1$ to $U_{T1}\lambda n$). Similarly, $U_{P2}$ represents a value for correcting a change due to light energy in the absorption spectrum of the second light absorber 216 of the second detection target 222. $U_{O2}$ represents a value for correcting a change due to oxidization in the absorption spectrum of the second light absorber 216 of the second detection target 222. $U_{T2}$ represents a value for correcting a change due to heat in the absorption spectrum of the second light absorber 216 of the second detection target 222. These correction values $U_{P2}$, $U_{O2}$, and $U_{T2}$ also exist for each wavelength in a predetermined wavelength band of light emitted from the light source 310 ($U_{P2}\lambda 1$ to $U_{P2}\lambda n$, $U_{O2}\lambda 1$ to $U_{O2}\lambda n$, $U_{T2}\lambda 1$ to $U_{T2}\lambda n$). Naturally, all of these six correction values need not be used, and a correction value need not be applied (made 0) if there is no influence of light energy, or oxidization, or heat, or if the influence thereof is negligible.

Methods for determining each of the correction values $U_{Pn}$, $U_{On}$, and $U_{Tn}$ in the present embodiment are described hereunder.

(Method 1: Arrangement of Reference Light Absorber)

According to method 1, a reference light absorber is arranged in an environment that is equivalent to the environment of the detection target 220, or is arranged in an environment with which the environment of the detection target 220 can be estimated. The amount of change in the absorption spectrum of the light absorber 214 of the detection target 220 is then computed by measuring the absorption spectrum of the reference light absorber. For example, if the reference light absorber is arranged in an equivalent environment, the computed amount of change is adopted as a correction value. For example, if the reference light absorber is arranged in an environment with which the environment of the detection target 220 can be estimated, a correction value is determined based on the computed amount of change. Note that, the phrase "environment with which the environment of the detection target 220 can be estimated" refers to, for example, an environment in which a known light intensity (for example, a light intensity of 20%) of the detection target 220 is applied.

Figure 14:
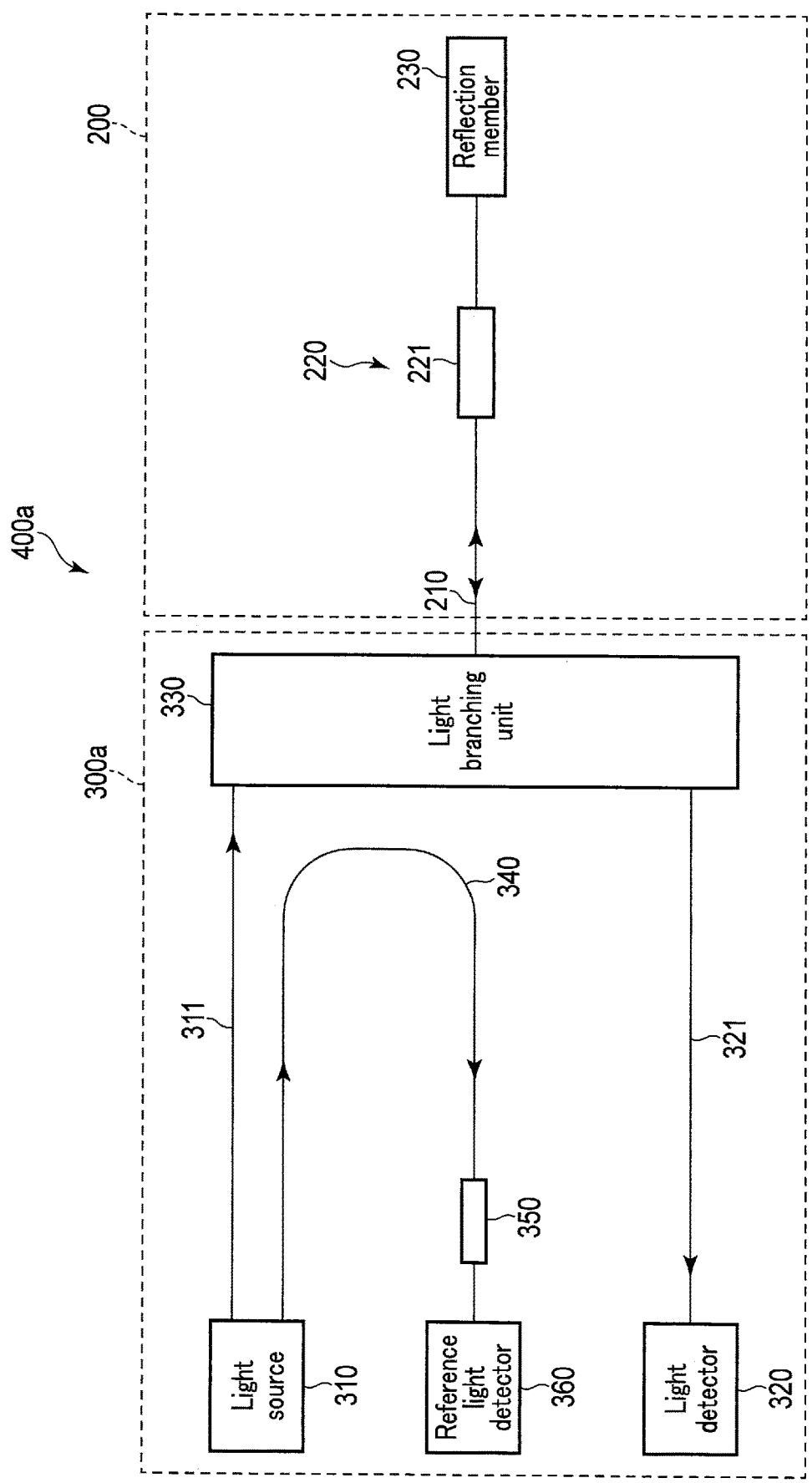
FIG. 14 is a view that schematically illustrates an example of a configuration for determining a correction value for correcting changes over time in the absorption spectrum of a light absorber of a detection target.

FIG. 14 is a view that schematically illustrates an example of a configuration for determining a correction value for correcting changes over time in the absorption spectrum of the light absorber of the detection target 220. In this example, a correction value for correcting changes over time in the absorption spectrum of the light absorber of the detection target 220 is determined by means of a fiber sensor 400*a* that comprises the sensor 200 and a sensor controller 300*a*.

In addition to the light source 310, the light detector 320, and the light branching unit 330, which are the same as the components described in the first embodiment, the sensor controller 300*a* of the fiber sensor 400*a* includes, for example, a light guide 340 that is an optical fiber that has flexibility, a detection target 350 that is provided in the light guide 340, and a reference light detector 360. The proximal end of the light guide 340 is connected to the light source 310, and the distal end is connected to the reference light detector 360. The detection target 350 provided in the light guide 340 has the same configuration as the detection target 220 provided in the light guide 210. That is, the detection target 350 includes a reference light absorber configured to absorb light of a predetermined wavelength band that is emitted from the light source 310 and guided through the light guide 340. The reference light absorber is of the same kind as the light absorber of the detection target 220. Similarly to the light detector 320, the reference light detector 360 is a detection element configured to acquire a light intensity for each wavelength (wavelength band), and includes a combination of a light receiving element and a color filter, a spectroscope, or the like. Detected light quantity information that is detected by the reference light detector 360 is output to the controller 100, similarly to the detected light quantity information that is detected by the light detector 320.

Changes over time in the light absorber that are due to light energy, oxidization, or heat applied to the detection target 220 occur gradually in comparison to the time period of a single usage of the endoscope (several hours at the longest). Therefore, it suffices to acquire a correction value at a time when the endoscope 30 is connected to the bend information computation apparatus 10, for example, when the light branching unit 330 of the sensor controller 300 and the light guide 210 of the sensor 200 are connected. Such acquisition of a correction value is performed by, for example, the controller 100, and the acquired correction value is stored in the storage 120, for example. Alternatively, a correction value may be acquired separately, and the acquired correction value may be input from the input device 50 and stored in the storage 120. Further, in a case where more precise correction is required, a correction value may be acquired at fixed time intervals, such as every 30 minutes.

Note that, apart from having the same form as the detection target 220 as illustrated in FIG. 14, the detection target 350 that includes a reference light absorber may be in the form of a filter that includes a transmission member that is coated on a glass plate and a reflection member that is coated on a mirror.

If an acquisition operation as described above is performed in a case where the detection target 350 that includes the reference light absorber is of the same form as the detection target 220 and is disposed in the same environment as the detection target 220, the amount of change in the absorption spectrum of the reference light absorber is adopted as the correction value. Further, if the reference light absorber has a filter-like structure or if the environment is one with which the environment of the detection target can be estimated, the amount of change in the absorption spectrum of the reference light absorber that is acquired is stored in the storage 120, and the bend information arithmetic operator 130 determines the correction value by converting from the acquired amount of change.

According to this method 1, the bend information arithmetic operator 130 of the controller 100 obtains a correction value by, for example, acquiring the absorption spectrum of the reference light absorber of the detection target 350 using the light detector 320 such as a spectroscope, and determining the amount of change in the acquired absorption spectrum relative to the absorption spectrum in an initial state (for example, at the time of factory shipment). The bend information arithmetic operator 130 then uses the obtained correction value to calculate bend information of the detection target 220 based on the aforementioned equation (6) by the same procedure as in the first to third embodiments.

Although in the above description an example is described in which a reference light absorber that corresponds to one detection target 220 of the sensor 200 is provided, hereunder an example is described in which reference light absorbers corresponding to all of the detection targets 220 (221 to 22*m*) are provided.

(Method 1-1: Arrangement of One Reference Light Absorber (One Color) in One Light Guide)

FIG. 15 is a view that schematically illustrates an example of a configuration for determining correction values for correcting changes over time in the absorption spectrums of light absorbers of the detection targets 220 (two detection targets 221 and 222). In this example, correction values for correcting changes over time in the absorption spectrums of the light absorbers of the detection targets 220 are determined by means of a fiber sensor 400*b* that comprises the sensor 200 and a sensor controller 300*b*.

In addition to the light source 310, the light detector 320 and the light branching unit 330 that are the same as the components described in the first embodiment, the sensor controller 300*b* of the fiber sensor 400*b* includes, for example, a light guide 340*b* including light guides 341 and 342 that are optical fibers that have flexibility, a detection target 350*b* including detection targets 351 and 352 that are provided in the light guides 341 and 342, the reference light detector 360 and an optical path switching element 370. The proximal ends of the light guides 341 and 342 are connected to the light source 310, and the distal ends are connected to the optical path switching element 370. The detection target 351 provided in the light guide 341 has the same configuration as the first detection target 221 provided in the light guide 210, and the detection target 352 has the same configuration as the second detection target 222. That is, the detection targets 351 and 352 each include a reference light absorber configured to absorb light of a predetermined wavelength band that is emitted from the light source 310 and guided through the light guides 341 and 342, respectively. The reference light absorbers of the detection targets 351 and 352 are of the same kind as the light absorbers of the detection targets 221 and 222, respectively, and are different from each other. Similarly to the light detector 320, the reference light detector 360 is a detection element configured to acquire a light intensity for each wavelength (wavelength band), and includes a combination of a light receiving element and a color filter, a spectroscope, or the like. Detected light quantity information that is detected by the reference light detector 360 is output to the controller 100, similarly to the detected light quantity information that is detected by the light detector 320.

The optical path switching element 370 switches the optical path of light from the light guides 341 and 342. By adopting this configuration, even when the two light guides 341 and 342 are provided, only one reference light detector 360 is needed. Accordingly, the number of reference light detectors 360 is reduced.

Naturally, the reference light detector 360 may be provided at the distal end of each of the light guides 341 and 342, respectively. By adopting such a configuration, the optical path switching element 370 is not required, and switching of optical paths is also not required.

Alternatively, optical paths may be switched using the light detector 320. When such a configuration is adopted also, the number of light detectors arranged in the fiber sensor 400b is reduced. Further, the influence of the sensitivity of the light detectors need not be taken into consideration.

In a case where the form of the detection targets 350 (351, 352) including the reference light absorbers is the same as the form of the detection targets 220 (221, 222), in the same manner as described above with respect to the first embodiment, the absorption spectrums of the reference light absorbers are acquired in a state in which the fiber sensor 400 is fixed in a predetermined shape, for example, a linear shape, and cannot bend. Naturally, the absorption spectrums of the reference light absorbers may be acquired in a predetermined shape other than a linear shape.

In a case where the reference light absorbers have the form of a filter, the absorption spectrums are measured at a place with a predetermined coating thickness in the respective reference light absorbers (in a state in which a change over time has not occurred, the quantity of light that is absorbed does not change if the coating thickness is constant). The number of places with a predetermined coating thickness at which the absorption spectrum is measured may be one place, or the absorption spectrum may be measured at places having the same coating thickness and the measurement values may be averaged. Alternatively, the absorption spectrum may be measured at places having different coating thicknesses, and a correction value may be determined based on a difference between the measurement values. Alternatively, a correction value may be determined based on a difference between the coloring material concentration of the light absorbers, or based on a difference between the numbers of filters in filter structures.

(Method 1-2: Arrangement of Reference Light Absorbers (Multiple Colors) in a Single Light Guide)

FIG. 16 is a view that schematically illustrates an example of a configuration for determining correction values for correcting changes over time in the absorption spectrums of light absorbers of the detection targets 220 (detection target 221 to 22m). In this example, correction values for correcting changes over time in the absorption spectrums of the light absorbers of the detection targets 220 are determined by means of a fiber sensor 400c that comprises the sensor 200 and a sensor controller 300c.

In addition to the light source 310, the light detector 320 and the light branching unit 330 that are the same as the components described in the first embodiment, the sensor controller 300c of the fiber sensor 400c includes, for example, a light guide 340c that is an optical fiber that has flexibility, detection targets 350c that are provided in the light guide 340c, and the reference light detector 360. The proximal end of the light guide 340c is connected to the light source 310, and the distal end is connected to the reference light detector 360. In FIG. 16, the single light guide 340c is provided with the detection targets 350c that include eight detection targets 351 to 358 corresponding to eight detection targets 221 to 22m (m=8) that are provided in the light guide 210 of the sensor 200c. Each of the detection targets 351 to 358 has the same configuration as the first to $m^{th}$ detection targets 221 to 22m provided in the light guide 210. That is, the detection targets 351 to 35m each include a reference light absorber configured to absorb light of a predetermined wavelength band that is emitted from the light source 310 and guided through the light guide 340c. The reference light absorbers of the detection targets 351 to 358 are of the same kind as the light absorbers of the detection targets 221 and 22m, respectively, and are different from each other.

Naturally, the number of light guides 340c is not limited to one, and two of the light guides 340c may be provided in which four detection targets (reference light absorbers) are arranged in each light guide 340c.

In this configuration also, the absorption spectrum of a reference light absorber is acquired by the reference light detector 360 by fixing all of the detection targets 350c including the reference light absorbers that are arranged in the same light guide 340c in a predetermined shape, for example, a linear shape, and thereafter causing only the detection target that is the measurement object to bend. Subsequently, the bend information arithmetic operator 130 calculates a correction value by determining the amount of change in the absorption spectrum based on the acquired absorption spectrum.

Although in the above methods 1-1 and 1-2, reference light absorbers that correspond to all of the detection targets 220 (221 to 22m) are prepared, in the following method 1-3, only reference light absorbers (some representative colors) that correspond to some of the detection targets 220 are prepared.

(Method 1-3: Arrangement of Only Some Reference Light Absorbers)

In method 1-3, as a premise it is assumed that the relation between changes over time among each reference light absorber (each color) is known, and that a change in a second color and a third color can be estimated based on a change in a first color. For example, a relational equation for estimating changes is stored in advance in the storage 120 of the controller 100, or is input from the input unit 110. Then, for example, the arithmetic operator 101 of the controller 100 uses the relational equation for estimating changes to determine the correction value for a light absorber that has not been prepared.

For example, in a case where there are eight colors, the reference light detector of the sensor controller measures changes in the absorption spectrums of two of the colors. The arithmetic operator 101 then calculates the changes in the absorption spectrums of the other colors by estimation based on the aforementioned changes in the absorption spectrums of the two colors. The arithmetic operator 101 then determines correction values for correcting changes over time in the absorption spectrums of the light absorbers of the detection targets 220.

Note that, as a representative color whose absorption spectrum is measured, a coloring material for which the influence of a change over time is easy to evaluate may be used, and the representative color need not be the color of a coloring material that is actually used in a light absorber of a detection target. Naturally, it is taken as a premise that the relation between changes over time in the respective coloring materials is known.

According to method 1-3, since it is not necessary to provide reference light absorbers corresponding to all of the detection targets 220, the configuration for determining a correction value can be simplified.

(Method 2: Determining a Correction Value by Estimation)

According to method 2, reference light absorbers are not provided, and the respective correction values $U_{Pn}$, $U_{On}$, and $U_{Tn}$ are determined by estimation.

FIG. 17 is a view that schematically illustrates an example of an endoscope system 1d that includes a bend information computation apparatus 10d for determining a correction value for correcting changes over time in the absorption spectrum of a light absorber of the detection target 220. The bend information computation apparatus 10d includes a fiber sensor 400d that comprises the sensor 200 and a sensor controller 300d. In addition to the sensor light source 310 and the light detector 320, the sensor controller 300d includes a cumulative driving time measurement unit 381, a light intensity measurement unit 382, and an elapsed time measurement unit 383. The cumulative driving time measurement unit 381 is, for example, an hour meter. The light intensity measurement unit 382 is, for example, an optical power meter. The elapsed time measurement unit 383 is, for example, a clock.

A storage 33 is provided in the control section 32 of the endoscope 30d. Information regarding the manufacturing date of the endoscope 30d, information regarding the number of times the endoscope 30d has been used, and the like are stored in the storage 33.

A temperature sensor 500 is disposed in the light guide 210 of the sensor 200. Preferably, the temperature sensor 500 is disposed in the vicinity of the detection target 220.

A change in an absorption spectrum that is caused by light energy can be estimated based on the integrated amount of light energy received. That is, the arithmetic operator 101 of the controller 100 calculates a correction value $U_{Pn}$ for correcting a change in the absorption spectrum caused by light energy, based on the light intensity of the light source 310 that is measured by the light intensity measurement unit 382 or the drive current of the light source 310 measured by an unshown ampere meter (or an instructed value from the controller 100), the cumulative driving time that is measured by the cumulative driving time measurement unit 381, and information stored in the storage 33. The calculated correction value $U_{Pn}$ is stored in the storage 120 and is used for computation of bend information by the bend information arithmetic operator 130.

A change in the absorption spectrum that is caused by oxidization can be estimated based on the elapsed time from the time of manufacture. That is, the arithmetic operator 101 of the controller 100 estimates the elapsed time from the time of manufacture based on information of the elapsed time measurement unit 383 that measures the elapsed time from the time of manufacture and information of the storage 33 of the endoscope 30d, and calculates a correction value $U_{On}$ for correcting the change in the absorption spectrum caused by oxidization. The calculated correction value $U_{On}$ is also stored in the storage 120 and is used for computation of bend information by the bend information arithmetic operator 130.

A change in the absorption spectrum that is caused by heat can be estimated based on the integrated amount of heat received by the light absorber 214 of the detection target 220. That is, the arithmetic operator 101 of the controller 100 calculates a correction value $U_{Tn}$ for correcting a change in the absorption spectrum caused by oxidization based on the temperature in the vicinity of the detection target 220 that is measured by the temperature sensor 500, the cumulative driving time that is measured by the cumulative driving time measurement unit 381, and information stored in the storage 33. The calculated correction value $U_{Tn}$ is stored in the storage 120 and is used for computation of bend information by the bend information arithmetic operator 130.

Note that, in the fourth embodiment also, the controller 100 may be configured so that, in a case where a correction value exceeds a setting range, the controller 100 notifies the user audibly or visually to that effect by notification of an error code or notification of the fact that the computing accuracy has decreased.

As described above, according to the present embodiment, a bend information computation apparatus can be provided that can correctly compute bend information even in a case where changes over time occur in the absorption spectrum of the light absorber 214 provided in the detection target 220, by directly computing the influence that light energy, oxidization, or heat has on an absorption spectrum by measurement, or by indirectly computing such influence by estimation, and computing bend information based on a relational equation to which a correction value that is based on the aforementioned influence has been added.

While various embodiments of the present invention have been described above, the present invention is not limited to the foregoing embodiments, and various improvements and changes are possible without departing from the gist of the present invention. Further, although the respective embodiments have been described taking the endoscope system 1 as an example, it will be obvious to a person with ordinary skill in the art that the bend information computation apparatus is not limited to an endoscope and is applicable to various kinds of insertion apparatuses.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bend information computation apparatus, comprising:
a controller comprising hardware, the controller being configured to:
receive detected light quantity information that represents a relation between a wavelength in a predetermined wavelength band and a light quantity, the detected light quantity information being acquired by using a sensor including a light guide having at least one light absorber and configured to change a light quantity of light that is transmitted through the light guide according to a bent state of the light absorber to detect a light quantity of the light after a change; and
compute bend information that represents a bend direction and a bend magnitude of each light absorber based on the detected light quantity information, an absorption spectrum of each light absorber, a bend coefficient of each light absorber that varies according to a bend direction and a bend magnitude of each light absorber, and a unique characteristic value of each light absorber;
wherein the unique characteristic value including a value for a correction relating to the bend coefficient.

2. The bend information computation apparatus according to claim 1, wherein the unique characteristic value includes an absorption spectrum correction value for correcting the absorption spectrum.

3. The bend information computation apparatus according to claim 2, wherein the absorption spectrum correction value is computed by a reference light absorber.

4. The bend information computation apparatus according to claim 2, wherein the absorption spectrum correction value is computed based on at least one of an integrated light quantity received by the light absorber, an integrated heat quantity, and an exposure time in an oxygen atmosphere.

5. The bend information computation apparatus according to claim 2, wherein the sensor including:
a light source configured to emit light of the predetermined wavelength band into the light guide, and
a light detector configured to detect a spectrum of light that is emitted from the light source and is transmitted through the light guide,
wherein the controller being further configured to measure a cumulative driving time of the sensor, and
the absorption spectrum correction value is computed based on the measured cumulative driving time.

6. The bend information computation apparatus according to claim 2, wherein the sensor including:
a light source configured to emit light of the predetermined wavelength band into the light guide, and
a light detector configured to detect a spectrum of light that is emitted from the light source and is transmitted through the light guide,
wherein the controller being further configured to:
measure a light intensity of the light source, and
measure a cumulative driving time of the light source, and
the absorption spectrum correction value is calculated based on the measured light intensity and the measured cumulative driving time.

7. The bend information computation apparatus according to claim 2, further comprising a temperature sensor arranged in a vicinity of the at least one light absorber; and
wherein the sensor including:
a light source configured to emit light of the predetermined wavelength band into the light guide, and
a light detector configured to detect a spectrum of light that is emitted from the light source and is transmitted through the light guide,
the controller being further configured to measure a cumulative driving time of the light source, in order to measure an integrated heat quantity of the light absorber; and
the absorption spectrum correction value is calculated based on measurements obtained by the temperature sensor and the measured cumulative driving time.

8. The bend information computation apparatus according to claim 1, wherein the unique characteristic value is a detection target correction term comprising a bend coefficient of a virtual detection target and an absorption spectrum of a light absorber at the virtual detection target.

9. The bend information computation apparatus according to claim 1, wherein the unique characteristic value is an absorption spectrum correction value for correcting the absorption spectrum, and a detection target correction term comprising a bend coefficient of a virtual detection target and an absorption spectrum of the virtual detection target.

10. The bend information computation apparatus according to claim 1, wherein the sensor including:
a light source configured to emit light of the predetermined wavelength band into the light guide, and
a light detector configured to detect a spectrum of light that is emitted from the light source and is transmitted through the light guide.

11. The bend information computation apparatus according to claim 1, wherein the controller is configured to, notify a user when at least one of a correction value and a correction term exceed a setting range.

12. An endoscope system, comprising:
an insertion section incorporated with a light guide having at least one light absorber, configured to change a light quantity of light that is transmitted through the light guide according to a bent state of the light absorber;
a sensor configured to detect a light quantity of the light after a change; and
a controller comprising hardware, the controller being configured to:
receive detected light quantity information that represents a relation between a wavelength in a predetermined wavelength band and a light quantity that is acquired by the sensor; and
compute bend information that represents a bend direction and a bend magnitude of each light absorber based on an absorption spectrum of each light absorber, a bend coefficient of each light absorber that varies according to a bend direction and a bend magnitude of each light absorber, and a unique characteristic value of each light absorber;
wherein the unique characteristic value including a value for a correction relating to the bend coefficient.

13. A bend information computation method, comprising:
acquiring detected light quantity information that represents a relation between a wavelength in a predetermined wavelength band and a light quantity by using a sensor including a light guide having at least one light absorber and configured to change a light quantity of light that is transmitted through the light guide according to a bent state of the light absorber to detect a light quantity of the light after a change;
acquiring an absorption spectrum of each light absorber, a bend coefficient of each light absorber that varies according to a bend direction and a bend magnitude of each light absorber, and a unique characteristic value of each light absorber; and computing bend information that represents a bend direction and a bend magnitude of each light absorber based on the detected light quantity information, the absorption spectrum, the bend coefficient, and the unique characteristic value;

wherein the unique characteristic value including a value for a correction relating to the bend coefficient.

14. The bend information computation method according to claim 13, wherein the unique characteristic value includes an absorption spectrum correction value for correcting the absorption spectrum.

15. The bend information computation method according to claim 14, further comprising measuring a cumulative driving time of the sensor, wherein the absorption spectrum correction value is computed based on the measured cumulative driving time.

16. The bend information computation method according to claim 14, further comprising:

measuring a light intensity of a light source, and measuring a cumulative driving time of the light source, wherein the absorption spectrum correction value is calculated based on the measured light intensity and the measured cumulative driving time.

17. The bend information computation method according to claim 14, further comprising:

measuring an integrated heat quantity of a light absorber, and measuring a cumulative driving time of a light source, wherein an absorption spectrum correction value is calculated based on the measured integrated heat quantity and the measured cumulative driving time.

18. The bend information computation method according to claim 13, wherein the unique characteristic value is a light absorber correction term comprising a bend coefficient of a virtual detection target and an absorption spectrum of a light absorber at the virtual detection target.

19. The bend information computation method according to claim 13, wherein the unique characteristic value is an absorption spectrum correction value for correcting the absorption spectrum, and a detection target correction term comprising a bend coefficient of a virtual detection target and an absorption spectrum of the virtual detection target.

20. The bend information computation method according to claim 13, wherein an absorption spectrum correction value is computed by a reference light absorber.

* * * * *